(12) United States Patent
Nichols

(10) Patent No.: US 6,382,035 B1
(45) Date of Patent: May 7, 2002

(54) MULTI-VALVING SAMPLE INJECTION APPARATUS

(75) Inventor: Jon A. Nichols, Forestville, CA (US)

(73) Assignee: Rheodyne, LP, Rhonert Park, CA (US)

( * ) Notice: Subject to any disclaimer, the term of this patent is extended or adjusted under 35 U.S.C. 154(b) by 0 days.

(21) Appl. No.: 09/824,865

(22) Filed: Apr. 2, 2001

(51) Int. Cl.⁷ .................................................. G01N 1/00
(52) U.S. Cl. .................................................. 73/863.72
(58) Field of Search ..................... 73/863.72, 863.73, 73/864.83, 864.84, 61.55, 61.56; 422/103

(56) References Cited

U.S. PATENT DOCUMENTS

| | | |
|---|---|---|
| 3,916,692 A | 11/1975 | Abrahams et al. |
| 3,918,913 A | 11/1975 | Stevenson et al. |
| 3,961,534 A | 6/1976 | Gundelfinger |
| 4,022,065 A | 5/1977 | Ramin et al. |
| 4,158,630 A | 6/1979 | Stearns |
| 4,242,909 A | 1/1981 | Gundelfinger |
| 4,625,569 A | 12/1986 | Toei et al. |
| 5,650,577 A | 7/1997 | Nagai et al. |

FOREIGN PATENT DOCUMENTS

| | | |
|---|---|---|
| EP | 327658 B1 | 10/1991 |
| JP | 3-175355 A | 7/1991 |

*Primary Examiner*—Robert Raevis
(74) *Attorney, Agent, or Firm*—Beyer Weaver & Thomas

(57) ABSTRACT

A multi-function valve apparatus for use with a Probe-In-Loop (PIL) architecture sample injection assembly which enables both Partial-Fill and Complete-Fill injections. The rotor element is rotatable about a rotation axis relative the stator between: a Load Position, an Overfill Position, and an Injection Position. In the Load Position, a first bridge channel fluidly couples a metering syringe to the sample loop assembly enabling the probe to aspirate one of a discrete volume of sample into the probe, during a Partial-Fill Mode, and a second volume of sample into the probe, during a Complete-Fill Mode. In the Overfill Position, in the Complete-Fill Mode, a second bridge channel fluidly couples a downstream loop portion to a waste port, and the first bridge channel fluidly couples the metering syringe to an upstream loop portion of the sample loop assembly. This enables the metering pump to dispense the sample from the probe into the downstream loop portion and out the waste port to completely fill the downstream loop portion and the second bridge channel with a substantially precise known volume. In the Injection Position, the second bridge channel fluidly couples the downstream loop portion to the analyzing device to inject the sample into the analyzing device, in either the Partial-Fill Mode or and the Complete-Fill Mode.

37 Claims, 28 Drawing Sheets

Fill mode: partial
Step: 5
Rotor position: C
Operation: ACTIVELY WASH PROBE

Fluid A
B
C
D

Fill mode: complete
Step: 8
Rotor position: B
Operation: MOVE TO B (SEAL LOWER LOOP)
          MOVE PROBE TO SAMPLE WASTE

MULTI-VALVING SAMPLE INJECTION APPARATUS

TECHNICAL FIELD

The present invention relates to sample injection apparatus, and more particularly, relates to multiple function sample valving apparatus for a Probe-In-Loop (PIL) sample injection assembly for liquid chromatographic analysis.

BACKGROUND ART

High Pressure Liquid Chromatography (HPLC) is a well known conventional technique in which liquid samples to be analyzed are injected under high pressure into a stream of solvent flowing through a chromatographic column. The sample size to be injected is usually several microliters in volume, but it may vary in size from less than 1 microliter up to 100 microliters or more. The pressure of the solvent stream into which the samples are injected may vary from less than 1000 psi up to 6000 psi or more.

Advances in Life Sciences, particularly in genomics and proteomics, have greatly increased the potential number of reactions and analyses that must be performed by the biotechnology and pharmaceutical industries. Thus, it is frequently necessary to analyze large numbers of samples routinely, even though the samples are available only in small quantities because they are difficult to isolate.

These tasks were formerly reserved for automatic sample injection devices made use of conventional 6-port sample injection valves with a sample loop which must be completely filled with the sample fluid. Typical of such devices are disclosed U.S. Pat. No. 3,918,913 to Stevenson & Coffey. While these designs provide high volumetric precision of the sample (typically in the range of 0.05–0.5% Relative Standard Deviation (RSD)), one problem associated with these "Complete-Loop Injection" systems is that they required an appreciable excess of sample to fill the sample loop reliably. Typically, four to five times the capacity of the sample loop are necessary for a reliable fill. Moreover, the excess sample liquid remaining in the connecting tubing between sample vial and valve would be discarded to make way for the next sample.

To address these deficiencies, micro syringe metering devices were employed to draw up a sample from a vial and introduce it into an injection valve with little or no loss of sample. Examples of these designs are U.S. Pat. No. 3,916,692 to Abraham et al.; U.S. Pat. No. 3,961,534 to Gundelfinger, and U.S. Pat. No. 4,022,065 to Ramin et al. These devices, however, are difficult to automate because the syringe has to be flushed several times between each injection in order to eliminate cross contamination.

Probe-In-Loop (PIL) automatic samplers were consequently developed which placed a docking port and needle probe intermediarily in the sample loop. This probe was adapted to undock from the docking port to aspirate a discrete volume of sample from a source into one portion of the sample loop, and then dock with the docking port to dispense this discrete volume into the other portion of the sample loop. These "Partial-Loop Injection" designs are advantageous to aspirate and dispense very small samples (<1 μl) with low dispersion. Further, unlike the "Complete-Loop Injection" designs, the probe tip of the PIL design may be easily undocked from the docking port for cleaning thereof to prevent cross-contamination. Typical of these PIL automatic samplers are disclosed in U.S. Pat. No. 4,242,909 to Gundelfinger, and European Patent No. EP327,658 to Strohmeier.

While these PIL automatic sampler designs provide the benefits of zero sample loss and rapid change of sample injection volume without any hardware changes, the injection volumes are relatively small. Moreover, the volumetric precision of the "Partial-Loop Injection" designs (typically in the range of 0.1–2.0% RSD), while good, is not as high as that of the "Complete-Loop Injection" designs.

Accordingly, it would be desirable to provide a PIL automatic sampler design which enables both Partial-Fill and Complete-Fill injections.

DISCLOSURE OF INVENTION

The present invention provides a multi-function valve apparatus for use with a Probe-In-Loop (PIL) architecture sample injection assembly, having a metering pump and an injection pump. The injection pump is configured to direct a Partial-Fill or a Complete-Fill of sample into a sample loop assembly, and to inject the sample from the sample loop assembly into an analyzing device. The sample loop assembly includes an upstream loop portion having one end connected to the valve and the other end coupled to a probe. The probe is adapted to aspirate a sample and hold it or to dispense the sample into a dock. The sample loop assembly further includes a downstream loop portion having an interior volume between the end coupled to the valve and the end coupled to the dock. The valve apparatus includes a stator element having a stator face defining a metering port fluidly coupled to the metering pump. The stator face further includes an injection pump port fluidly coupled to the injection pump, a loop upstream port fluidly coupled to one end of the upstream loop portion, and a loop downstream port fluidly coupled to one end of the downstream loop portion. An exit port is further provided fluidly coupled to the analyzing device. A waste port is coupled to a waste container. A rotor having a rotor face is included in fluid-tight contact against the stator face. The rotor face includes a first bridge channel, a second bridge channel defining a discrete volume with the stator face, and a third bridge channel.

The rotor face is rotatable about a rotation axis relative the stator between: a Load Position, an Overfill Position, and an Injection Position. In the Load Position, the first bridge channel fluidly couples the metering port to the sample loop upstream port enabling the probe to aspirate a discrete volume of sample into the probe, during a Partial-Fill Mode, and a second volume of sample into the probe, during a Complete-Fill Mode. In the Overfill Position, in the Complete-Fill Mode, the second bridge channel fluidly couples the sample loop downstream port to the waste port, and the first bridge channel fluidly couples the metering port to the sample loop upstream port. This enables the metering pump, when the probe is docked in the dock, to dispense the sample from the probe into the downstream loop portion, out of the downstream port, into the second bridge channel and out the waste port to completely fill the downstream loop portion and the second bridge channel with a substantially precise known volume. Finally, in the Injection Position, the second bridge channel fluidly couples the downstream loop port to the exit port, and the third bridge channel fluidly couples the injection pump port to the sample loop upstream port. This enables the injection pump, when the probe is docked in the dock, in both the Partial-Fill Mode and the Complete-Fill Mode, to inject the sample into the analyzing device.

Accordingly, a rotor valve assembly is provided for a Probe-In-Loop automatic sampling device which enables both Partial-Fill and Complete-Fill injections. Thus, this versatile automatic sampling device enables rapid change of injection volume with zero sample loss and without any hardware changes (i.e., "Partial-Loop Injection" designs), while further offering larger injection volumes with increased volumetric precision (i.e., "Complete-Loop Injection" designs).

In one embodiment, the waste port, the upstream port and the exit port lie on a first imaginary circle that is concentric with the rotation axis. The distal ends of the second bridge channel further lying on the imaginary circle such that, in the Overfill Position, one distal end fluidly connects to the waste port and the other distal end fluidly connects to the loop downstream port, and such that, in the Injection Position, the one distal end fluidly connects to the loop downstream port and the one distal end fluidly connects to the exit port.

In another embodiment, the stator face further defines a first communication channel having one end in fluid communication with the exit port and the other distal end lying on the first imaginary circle such that, in the Injection Position, the other end being in fluid communication with the other end of the second bridge channel. Further, the third bridge channel fluidly couples the injection pump port to the exit port enabling the injection pump to purge the analyzing device in a fourth valve position.

In yet another configuration, in a fifth valve position, the first bridge channel fluidly couples the metering port to a pump seals port to fluidly couple the metering pump to the pump seals of the injection pump for cleaning thereof. The metering port is centrally positioned substantially at the rotational axis, and the first bridge channel extends radially outward from the rotational axis. At the same time, the third bridge channel connects the injection pump port to the waste port, allowing the pump to dump its contents to waste.

In another aspect of the present invention, a Probe-In-Loop (PIL) architecture sample injection assembly is provided comprising a rotor valve assembly including a stator element and a rotor element. The stator element includes a stator face defining an injection pump port, a metering port, a loop upstream port, a loop downstream port, an exit port and a waste port. The rotor element includes a rotor face in fluid-tight contact against the stator face, and defines at least one bridge channel. The sample injection assembly further includes an injection pump fluidly coupled to the stator injection pump port for supplying mobile phase fluid, and a metering pump fluidly coupled to the stator metering port for supplying or withdrawing metered mobile phase fluid. An analyzing device is fluidly coupled to the stator exit port. A PIL sample loop is included having a docking station, a probe, an upstream loop portion and a downstream loop portion. The upstream loop portion is fluidly coupled to the loop upstream port of the stator element to permit aspiration of sample into the probe and dispensing of the aspirated sample from the probe into the dock. The downstream loop portion fluidly couples to the dock and to the loop downstream port of the stator element. The downstream loop portion has a discrete interior volume between the dock and the loop downstream port.

The rotor face is rotatable about a rotation axis relative to the stator between: a Load Position, an Overfill Position, and an Injection Position. In the Load Position, the metering port is fluidly coupled to the sample loop upstream port enabling the probe to aspirate a discrete volume of sample into the probe, during a Partial-Fill Mode, and a second volume of sample into the probe, during a Complete-Fill Mode. In the Overfill Position, in the Complete-Fill Mode, the sample loop downstream port is fluidly coupled to the waste port, and the metering port is fluidly coupled to the sample loop upstream port. This enables the metering pump, when the probe is docked in the docking station, to dispense the aspirated sample from the probe into the downstream loop portion, and out of the loop downstream port toward the waste port to completely fill the downstream loop portion with a substantially precise known volume. In the Injection Position, the sample loop downstream port is fluidly coupled to the exit port, and the injection pump port is fluidly coupled to the sample loop upstream port. This enables the injection pump, when the probe is docked in the dock, in both the Partial-Fill Mode and the Complete-Fill Mode, to inject the sample into the analyzing device.

The rotor valve assembly of the sample injection assembly includes a seal purge position which provides purging of the seals of the injection pump. Debris and other contaminants reducing seal longevity may be swept out of the chamber behind the rear seal by this function. Preferably, in the purge position, the metering device is fluidly coupled to this chamber of the injection pump for purging thereof.

In another aspect of the present invention, a method is provided for transferring sample from a sample source to an analyzing device using multi-function valve apparatus for use with a Probe-In-Loop (PIL) architecture sample injection assembly to direct a Partial-Fill or a Complete-Fill of the sample into a sample loop assembly, and to inject the sample from the sample loop assembly into the analyzing device. The method includes loading a discrete volume of sample through the probe, in the Partial-Fill Mode, and a second volume of sample through the probe, in the Complete-Fill Mode. In the Complete-Fill Mode when the probe is docked in the dock, fluidly coupling the sample loop downstream port to the waste port through the second bridge channel of the rotor. Then, dispensing a portion of the sample from the probe though the dock and into the downstream loop portion, out of the downstream port, into the second bridge channel and out the waste port to completely fill the downstream loop portion and the second bridge channel with a substantially precise known volume. The rotor then fluidly couples the sample loop downstream port to the exit port. Finally, injecting the discrete volume of sample, in the Partial-Fill Mode, or injecting the precise known volume of sample, in the Complete-Fill Mode, into the analyzing device.

BRIEF DESCRIPTION OF THE DRAWINGS

The assembly of the present invention has other objects and features of advantage which will be more readily apparent from the following description of the best mode of carrying out the invention and the appended claims, when taken in conjunction with the accompanying drawing, in which:

BEST MODE OF CARRYING OUT THE INVENTION

Figure 1:
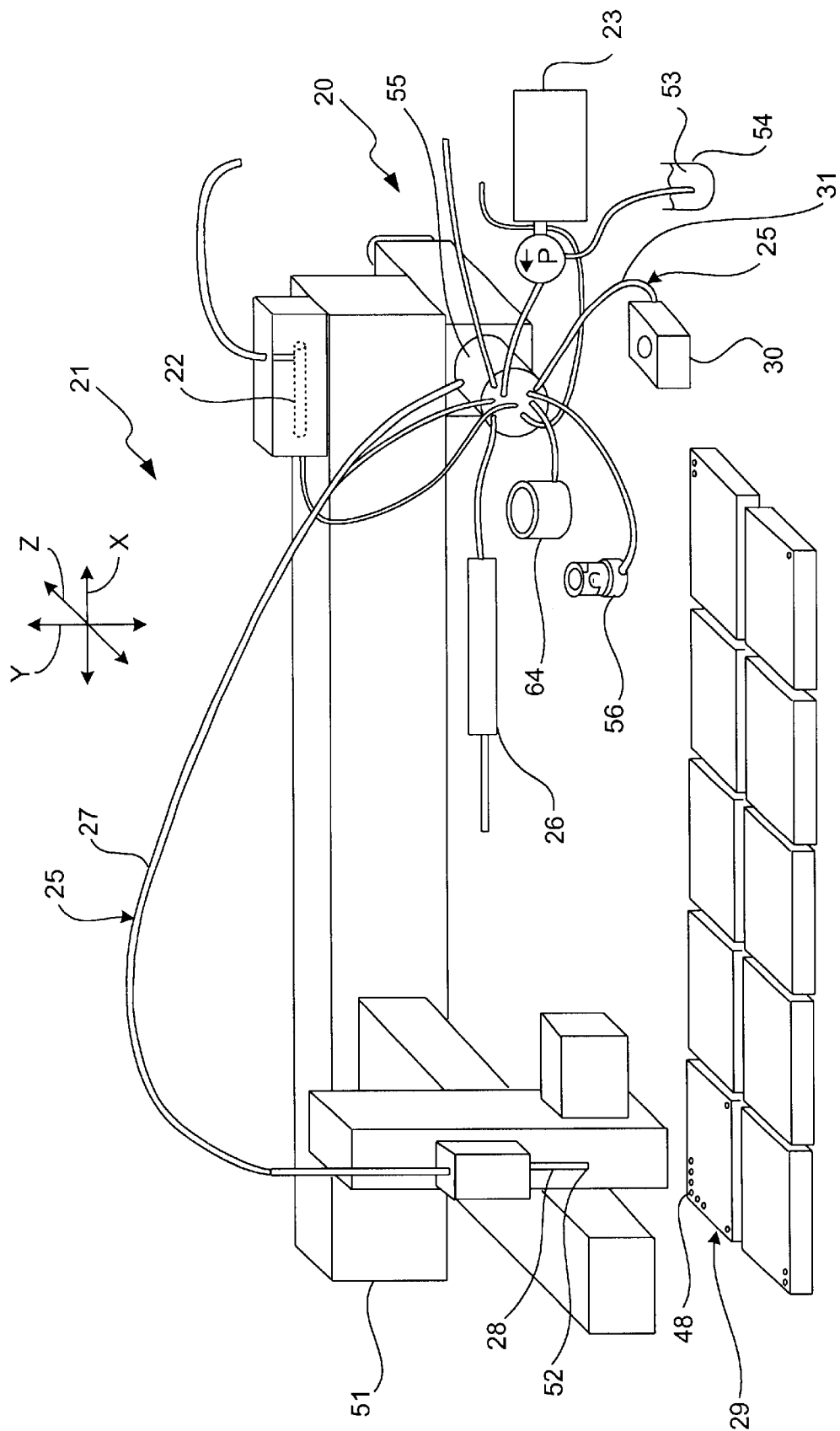
FIG. 1 is a top perspective view of the multi-valving sample injection system constructed in accordance with the present invention.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

Referring now to FIGS. 1–3, a multi-function valve apparatus, generally designated 20, is provided for use with a Probe-In-Loop (PIL) architecture sample injection assembly 21, having a metering pump 22 and an injection pump 23. The injection pump is configured to direct a Partial-Fill (FIGS. 2A–2J) or a Complete-Fill (FIGS. 3A–3N) of sample 24 into a sample loop 25, and to inject the sample from the sample loop into an analyzing device 26. The sample loop assembly 25 includes an upstream loop portion 27 coupled to a probe 28 and the valve. This probe is adapted to aspirate sample 24 from a sample source 29 therein, and to dispense the drawn sample 24 therefrom into a dock 30. The sample loop 25 further includes a downstream loop portion 31 having a discrete interior volume. The valve apparatus 20 includes a stator element (FIG. 4), generally designated 32, having a stator face 33 defining a metering port 35 fluidly coupled to the metering pump 22. The stator face 33 further includes an injection pump port 36 fluidly coupled to the injection pump 23, a loop upstream port 37 fluidly coupled to the upstream loop portion 27, and a loop downstream port 38 fluidly coupled to the downstream loop portion 31. An exit port 40 is further provided fluidly coupled to the analyzing device 26. Port 39 connects to a waste reservoir. A rotor element (FIG. 5), generally designated 41, includes a rotor face 42 in fluid-tight contact against the stator face 33. The rotor face 42 includes a first bridge channel 43, a second bridge channel 45 defining a discrete volume with the stator face 33, and a third bridge channel 46.

Figure 2A:
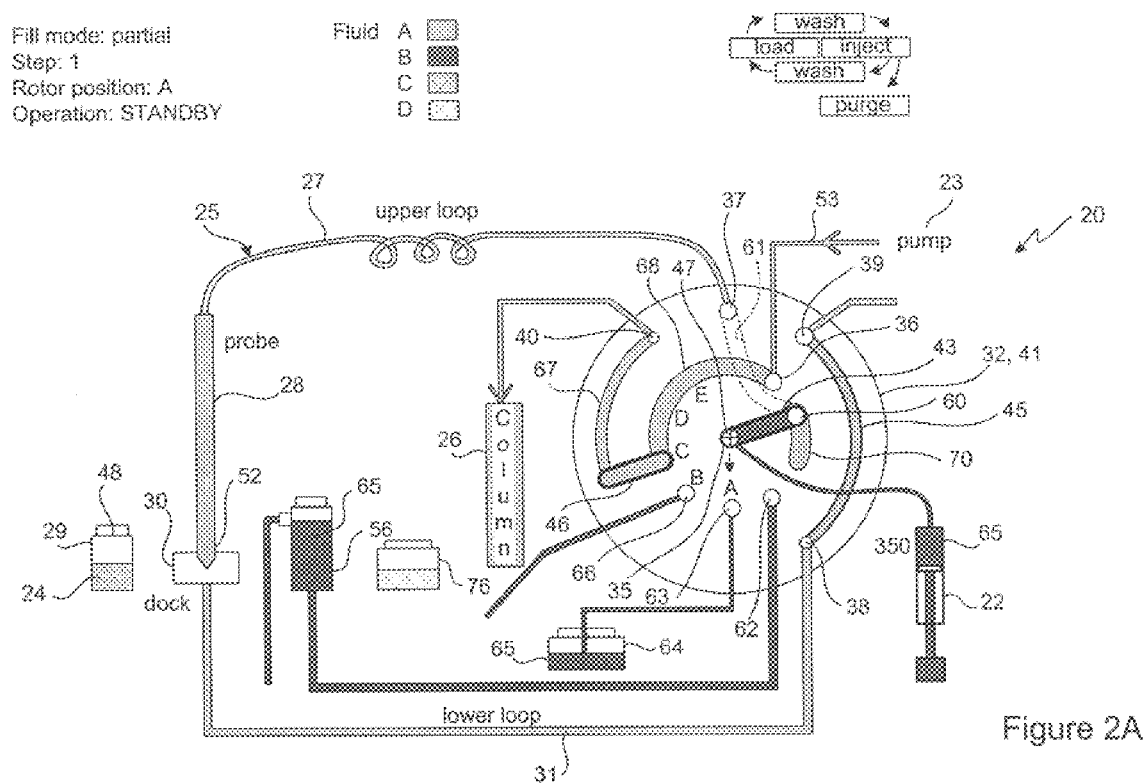
FIGS. 2A–2J is a series of schematic views of the rotor-stator interface, illustrating operation of the sample injection valve of FIG. 1, in the "Partial-Fill Mode".
Figure 2B:
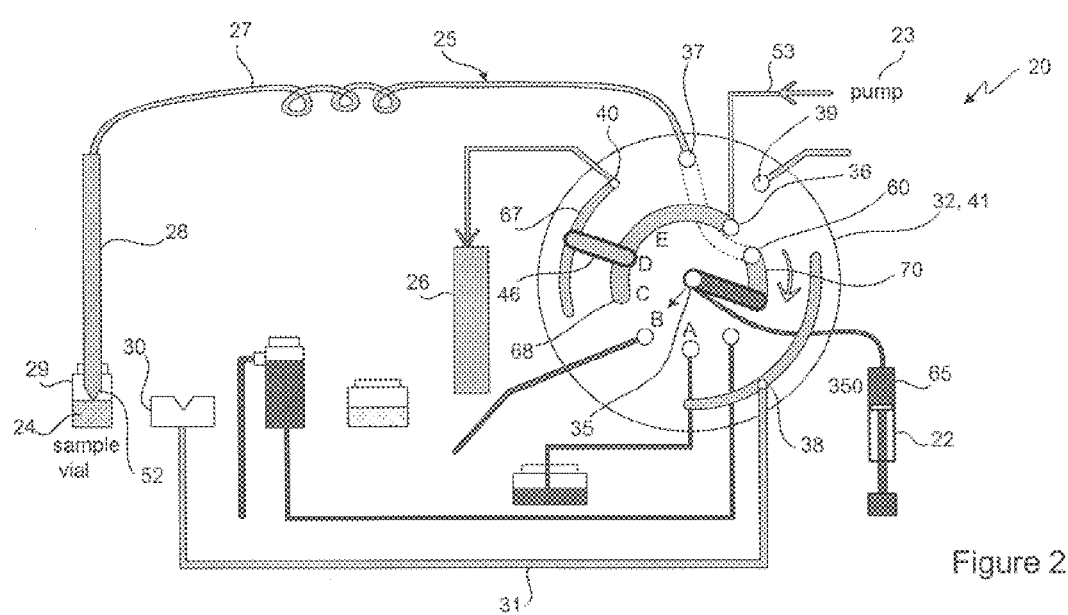
Figure 2C:
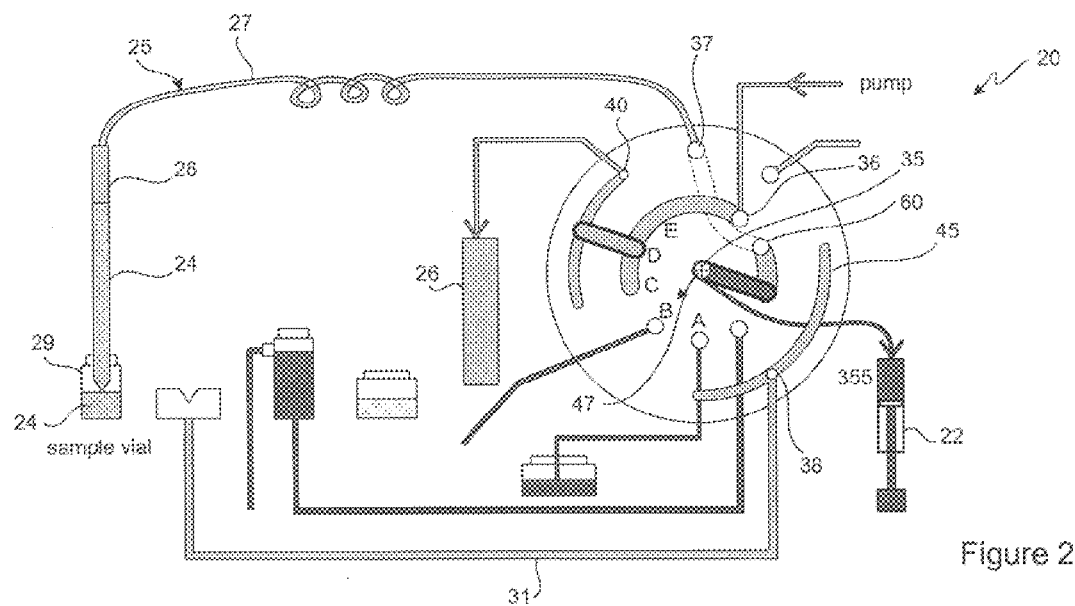
Figure 2D:
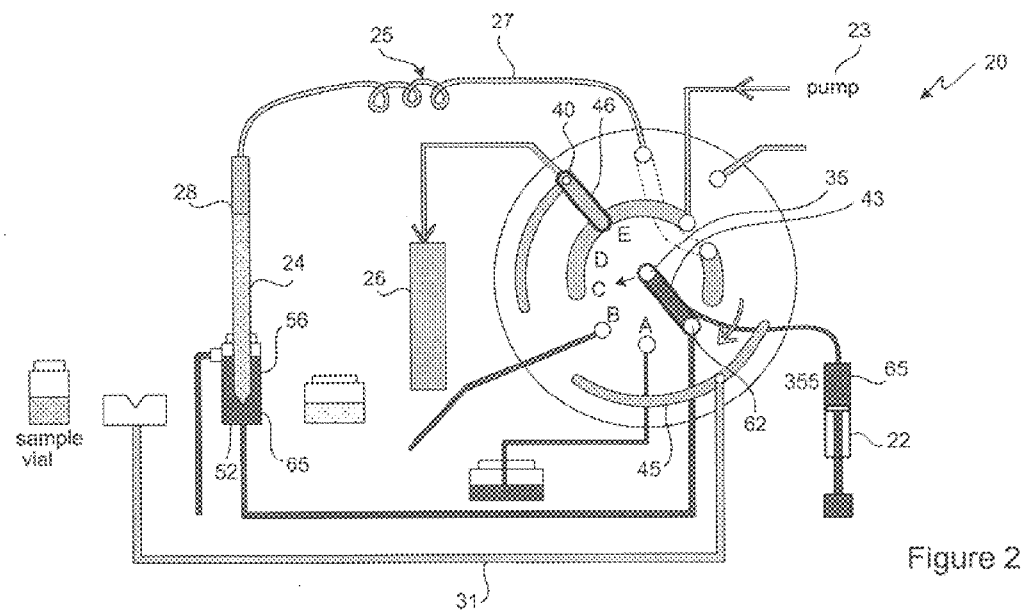
Figure 2E:
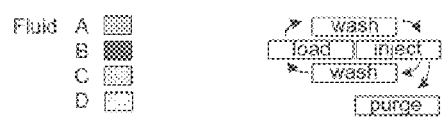
Figure 2E:
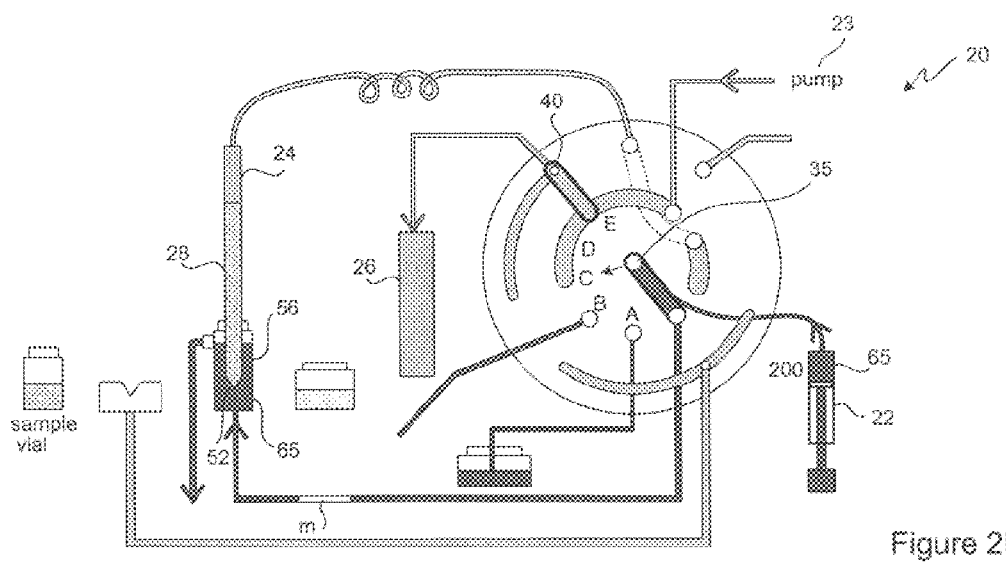
Figure 2F:
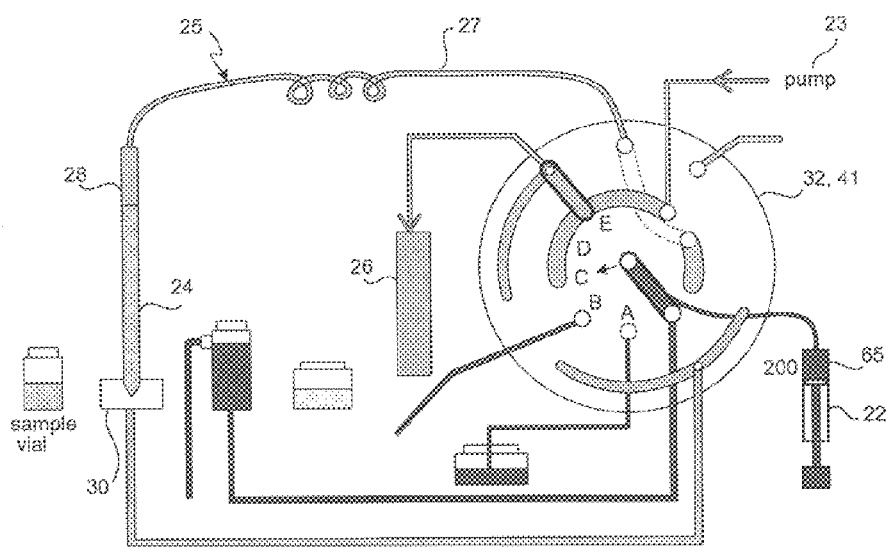

The rotor face 42 is rotatable about a rotation axis 47 relative to the stator element between: a Load Position (Rotor Position B (FIGS. 2C and 3C)), an Overfill Position (Rotor Position A (FIG. 3G)), and an Injection Position (Rotor Position D (FIGS. 2G and 3K)). In the Load Position, the first bridge channel 43 fluidly couples the metering port 35 to the loop upstream port 37 enabling the probe to aspirate a discrete volume of sample into the probe 28, in the Partial-Fill Mode (FIGS. 2A–2J), and a second volume of sample into the probe 28, in the Complete-Fill Mode (FIGS. 3A–3N). In the Overfill Position (FIG. 3G), only for the Complete-Fill Mode, the second bridge channel 45 fluidly couples the sample loop downstream port 38 to the waste port 39, and the first bridge channel 43 fluidly couples the metering port 35 to the sample loop upstream port 37. This enables the metering pump 22, when the probe 28 is docked in the docking station 30, to dispense the sample from the probe 28 into the dock end of the downstream loop portion 31, out of the downstream port 38, into the second bridge channel 45 and out the waste port 39 to completely fill the downstream loop portion 31 and the second bridge channel 45 with a substantially precise known volume. Finally, in the Injection Position (FIGS. 2G and 3K), the second bridge channel 45 fluidly couples the sample loop downstream port 38 to the exit port 40, and the third bridge channel 46 fluidly couples the injection pump port 36 to the sample loop upstream port 37. This enables the injection pump 23, when the probe 28 is docked in the docking station 30, to dispense the sample, in both the Partial-Fill Mode and the Complete-Fill Mode, into the sample loop downstream port 38 and into the analyzing device 26.

Accordingly, a rotor valve assembly is provided for a Probe-In-Loop (PIL) automatic sampling device which enables both Partial-Fill and Complete-Fill injections from the sample loop. This dual functionality adds substantial versatility to PIL automatic sampling devices. Unlike current designs, the present invention enables rapid changes of injection volume with zero sample loss and without any hardware changes (i.e., "Partial-Loop Injection" designs).

For example, one analysis may require 1 $\mu$L, and a subsequent analysis may require 10 $\mu$L. This volume variation may be performed without operator variation. Moreover, this system offers analysis with exceptionally high volumetric precision through fixed volume capabilities (i.e., "Complete-Loop Injection" designs).

Figure 3A:
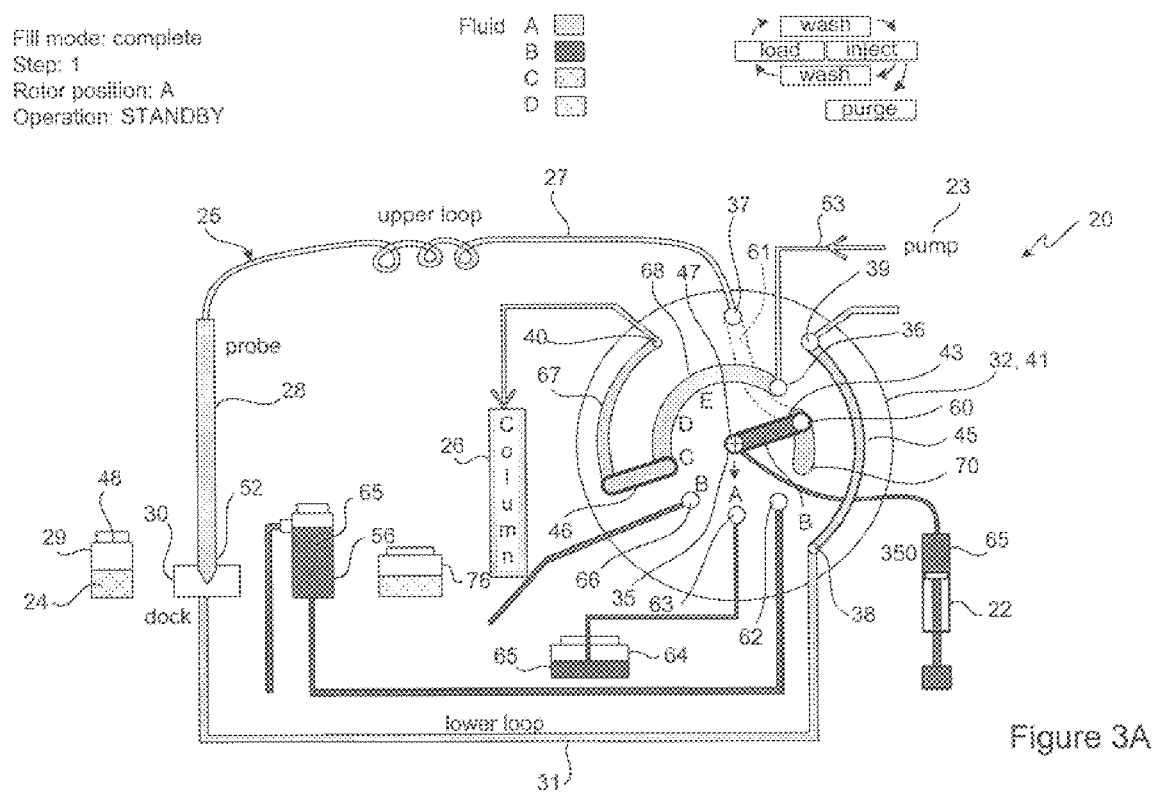
FIGS. 3A–3N is a series of schematic views of the rotor-stator interface, illustrating operation of the sample injection valve of FIG. 1, in the "Complete-Fill Mode".
Figure 3B:
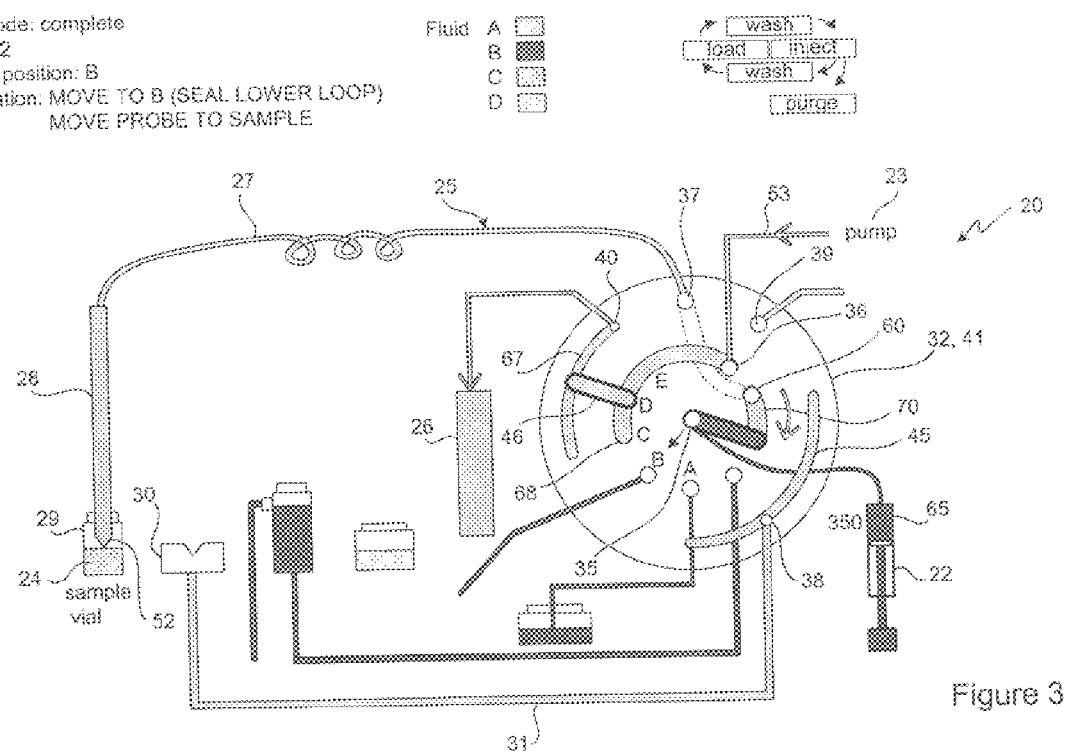

Briefly, the sample injection assembly 21 is illustrated in FIG. 1 which is designed to draw samples (i.e., sample source 29) from sample vials or an array of reservoir wells 48 of a conventional microtiter plate, i.e. 96 or 384 wells, and inject the drawn samples through chromatographic column or other analyzing device 26 for analysis thereof. Initially, a three-axis precision positioner 51 manipulates the tip 52 of the probe 28 down into a well 48, as shown in FIGS. 2B and 3B. In the Load Position, the rotor valve apparatus 20 fluidly couples the upstream sample loop portion 27 to the metering pump 22 so that either a small metered volume of sample or a substantially larger volume of sample (depending upon whether a Partial-Fill or Complete-Fill of the downstream loop portion 31 is desired) can be drawn from a well. The positioner 51 then manipulates the probe out of the well 48 and to the docking station 30. At the docking station 30, the probe 28 is moved down to press the probe tip against the dock to seat and seal thereagainst (FIGS. 2F and 3F).

Figure 2G:
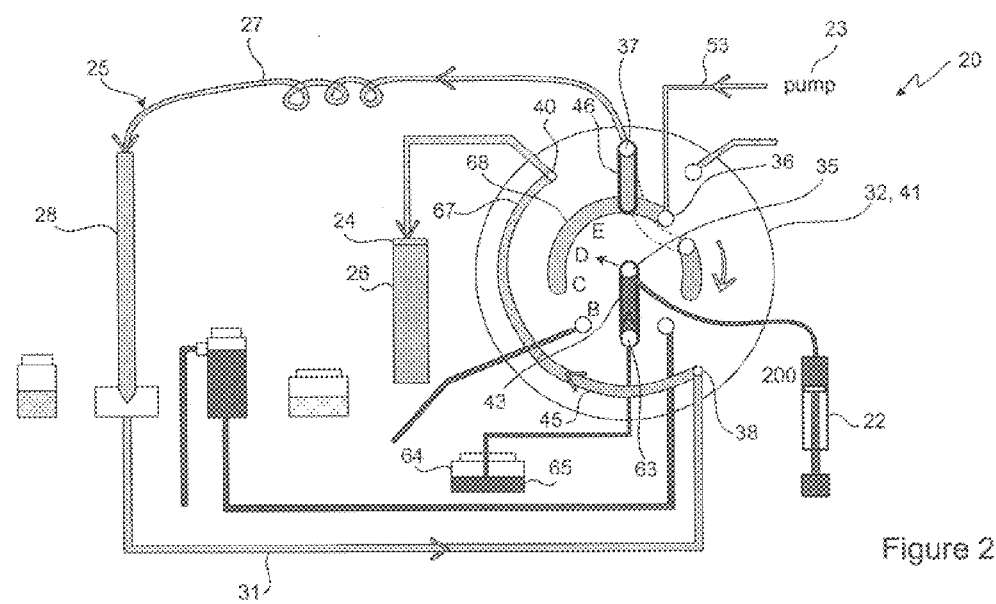

In the Partial-Fill Mode, as shown in FIGS. 2A–2J, the rotor valve apparatus 20 rotates the rotor element 41 to the Injection Position which fluidly couples the injection pump 23 to the upstream loop portion 27, and the downstream loop portion 31 to the analyzing device 26. The discrete volume of aspirated sample is then moved along the downstream loop portion 31, through the valve and directly into the analyzing device. This is preferably actuated by pumping mobile phase fluid (e.g., a mixture of water and acetonitrile) through the upstream loop portion 27, the probe 28, the docking station 30, and through the downstream loop portion 31 to inject the discrete volume of aspirated sample directly into the analyzing device (FIG. 2G). Accordingly, the smaller discrete volume of sample may be analyzed with zero waste.

In contrast, in the Complete-Fill Mode, as shown in FIGS. 3A–3N, the entire interior volume (i.e., a "Complete-Fill") of the downstream loop portion 31 is to be filled with sample. This provides the well known benefit of high volumetric precision, typically being in the range of about 0.05% to about 0.50% RSD, depending upon the interior volume of the downstream loop portion 31.

Thus, when the rotor valve assembly rotates the rotor element 41 to the Overfill Position (FIG. 3G), in the "Complete-Fill Mode", the injection pump 23 is similarly fluidly coupled to the upstream loop portion 23, but the downstream loop portion 31 is fluidly coupled to the waste port 39 positioned at the stator face 33. This enables the injection pump 23 to "over-fill" the downstream loop portion 31 by dispensing excess sample out of the waste port 39. Accordingly, the volume of the aspirated sample, in the "Complete-Fill" mode, must be greater than that of the interior volume of the downstream loop portion 31 to enable overfilling. Preferably, such overfill volume is four to five times that of the downstream loop portion 31.

To perform this overfill and completely fill the downstream loop portion 31 with a substantially more precise volume of sample than compared to the "Partial-Fill" mode, the mobile phase fluid is pumped, via the injection pump 23, through the upstream loop portion 27 until it is overfilled. While a sufficient volume of mobile phase fluid is required to dispense excess sample through the waste port 39 to a waste source, to maintain a "Complete-Fill" of the downstream loop portion 31, the mobile phase fluid is not be pumped into the downstream loop portion in the Overfill Position (FIG. 3G).

Figure 3C:
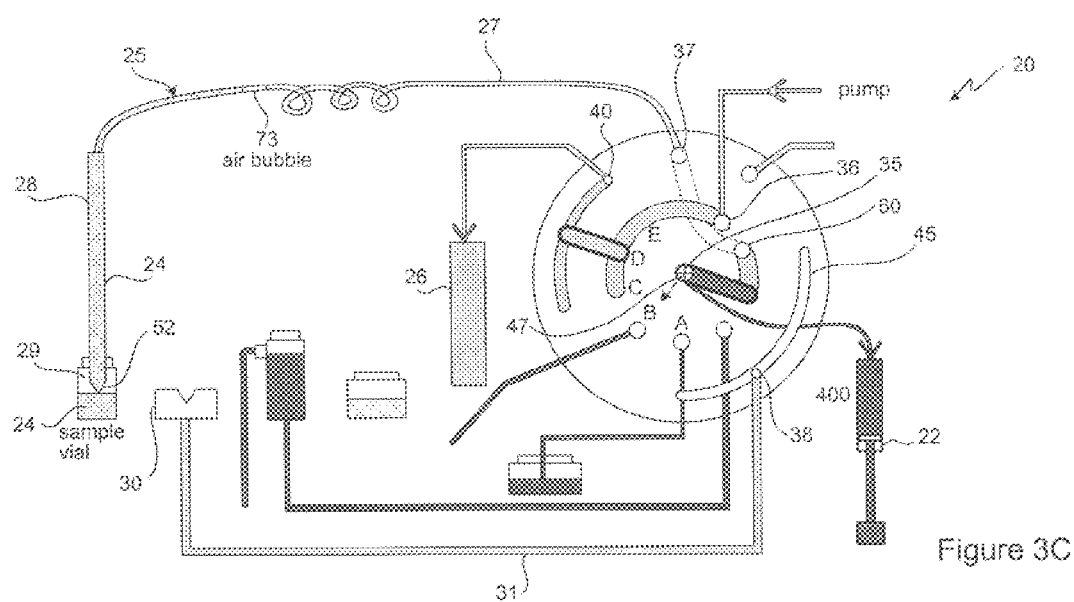
Figure 3D:
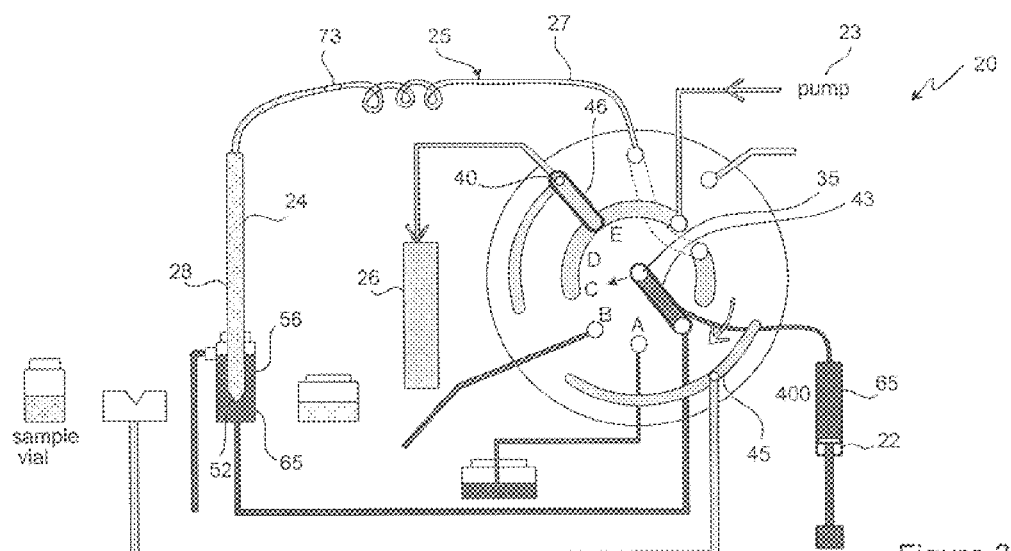
Figure 3E:
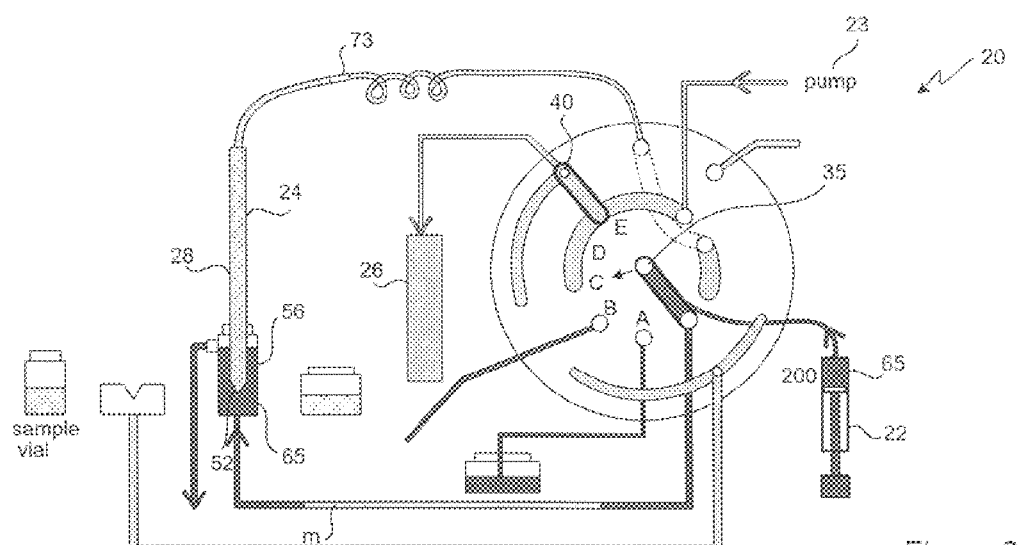
Figure 3F:
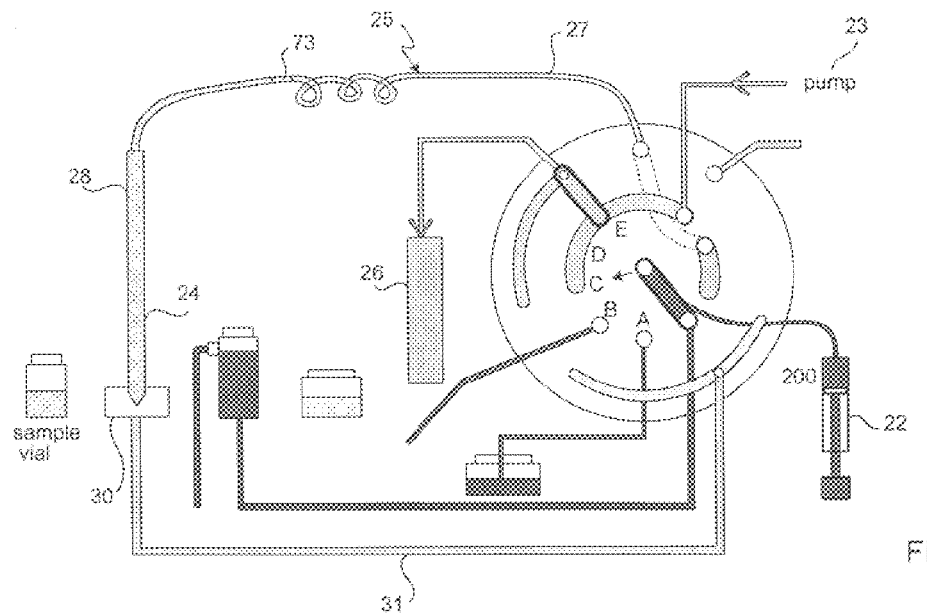
Figure 3G:
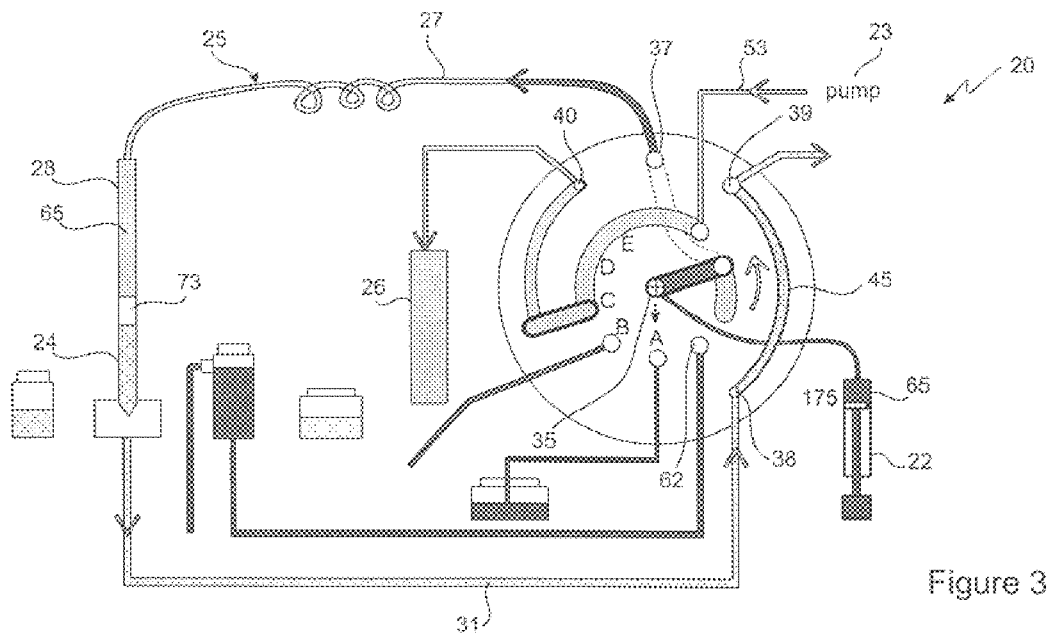
Figure 3H:
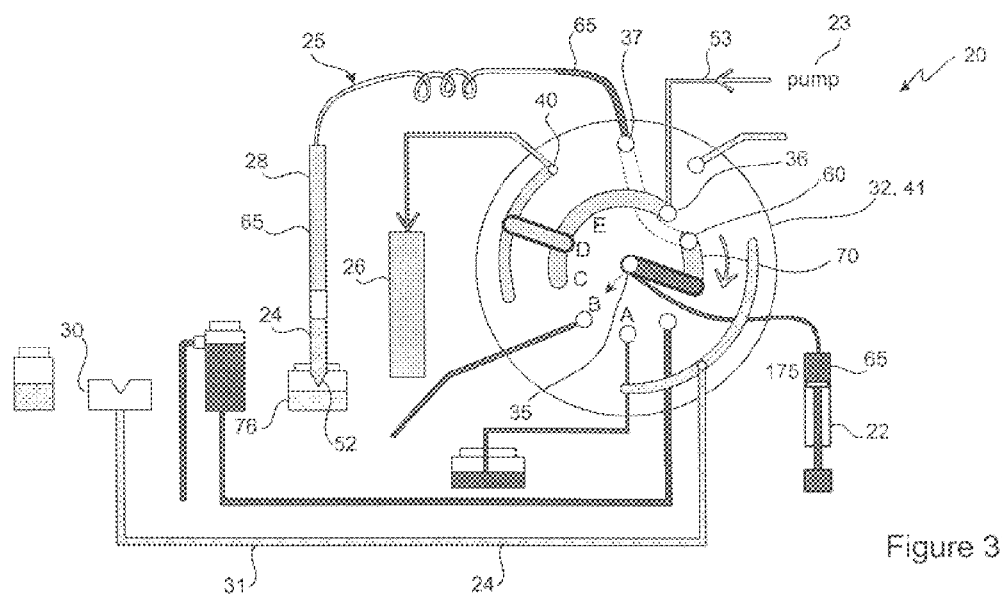
Figure 3I:
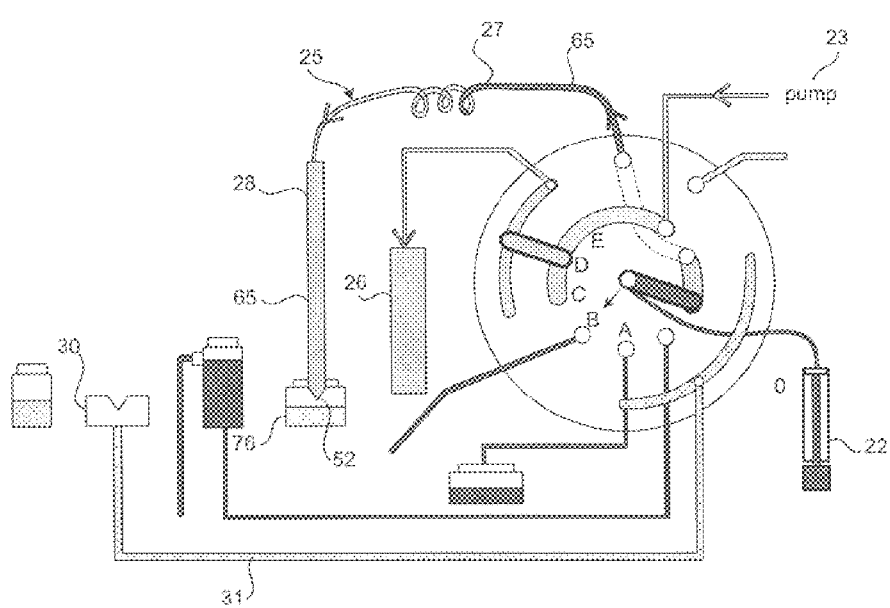
Figure 3J:
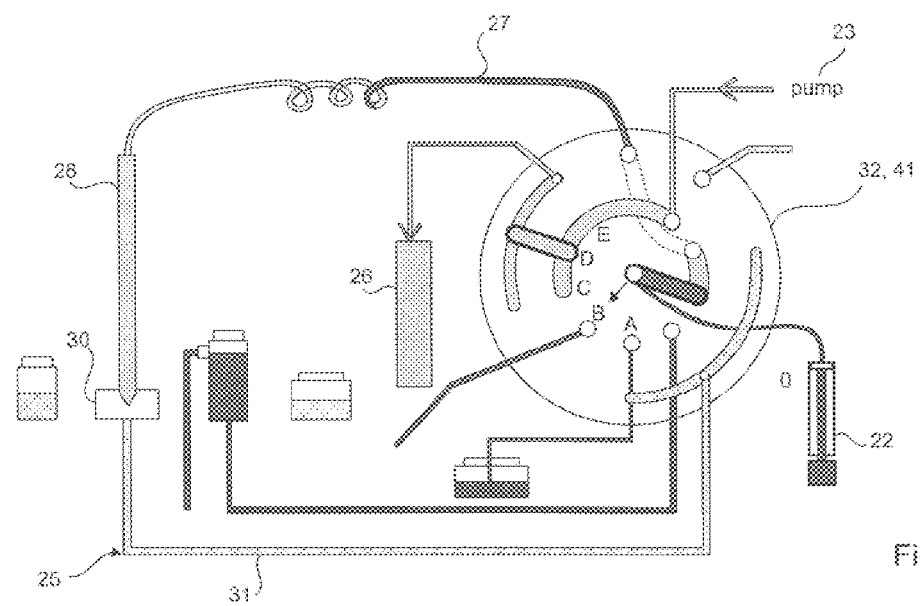
Figure 3K:
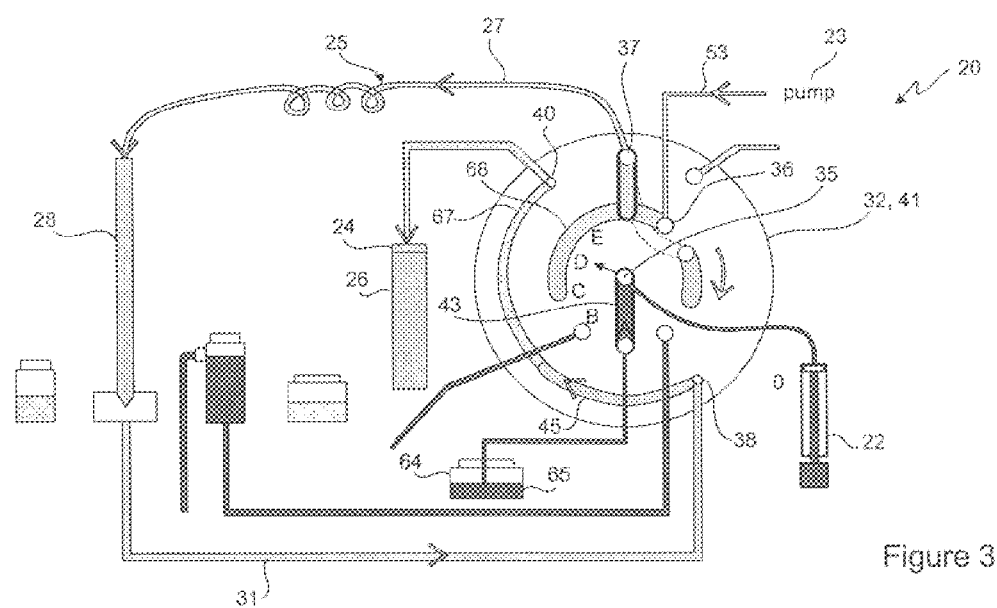

Subsequently, after completion of the overfill, and expulsion of the excess sample from probe 28 and upstream loop portion 27 (FIG. 3H (Rotor Position B), and as will be described below), the rotor valve assembly rotates the rotor element to the Injection Position (FIG. 3K). Similar to the Injection Position, in the "Partial-Fill" mode, the upstream loop portion 27 remains fluidly coupled to the injection pump 23, and the downstream loop portion 31 is then fluidly coupled to the analyzing device 26. The mobile phase fluid is then pumped through the upstream loop portion 27, the probe 28, the docking station 30, and through the downstream loop portion to inject the entire volume of the sample directly into the analyzing device.

Referring back to FIG. 1, several precision instruments are required to effect the sample injection. For example, the metering function is performed by a single motorized metering pump 22 which forms a vacuum or negative pressure at the probe tip 52, in the Load Position. Consequently, the predetermined volume of sample can be aspirated through the probe in either the "Partial-Fill" mode or the "Complete-Fill" mode. In contrast, the metering device may be utilized to generate a positive pressure for flushing and rinsing functions. As will be described in greater detail below, a positive pressure generated by the metering pump enables washing and rinsing of the probe tip 52 in the Washing Position (Rotor Position C (FIGS. 2D, 2E, and 3D, 3E)); and flushing of the injection pump seals in the Pump Seal Flush Position (Rotor Position E (FIG. 6)).

In the preferred form, the metering pump 22 is provided by a syringe-type pump or a diaphragm pump, or by a pressurized source delivering a positive or negative pressure to the probe 28. Typical of these aspiration devices is Model #2009D provided by Innovadyne Technologies, Inc., Rohnert Park, Calif.

Another precision instrument is the high pressure injection pump 23 which is generally applied to pump the mobile phase fluid 53 from a supply reservoir 54 to the valve apparatus 20 to flow fluid into the upstream loop portion 27. The mobile phase fluid 53 is thus pumped at a high pressure from a supply reservoir 54 to the rotor valve apparatus 20 and into the upstream loop portion 27. From there, the fluid passes through the docked probe 28, the docking station 30 and into the downstream loop portion 31 for injection of the sample through the analyzing device 26, via the rotor valve apparatus 20. Briefly, to maintain the analyzing device 26, which is preferably a chromatographic column, continuously filled with flowing mobile phase fluid when the sample is being aspirated, or after the sample as been injected in the analyzing device, the injection pump 23 can be more directly fluidly coupled to the analyzing device 26 through the exit port 40 at multiple positions (FIGS. 2A–2F, 2I and 2J (in the Partial-Fill Mode) and FIGS. 3A–3J, 2M and 3N (in the Complete-Fill Mode) corresponding to Rotor Positions A–C).

The injection pump 23 is preferably a high pressure pump typically delivering continuously, metered pressure ranging from about 1000 PSI to about 6000 PSI. Preferably, the injection pump 23 is provided by a conventional instrument supplier designed for HPLC. These devices are commercially available and well known in the art. For instance, the Waters Associates Model No. 600 which is suitable for use with the present invention may be employed.

Yet another precision instrument at the heart of the rotor valve apparatus 20 is the shear valve or flat face valve. Both the rotor element 41 (FIG. 5) and the stator element 32 (FIG. 4) are composed of conventional shear valve or flat face valve materials which are adapted to support the high pressure contact at the stator-rotor interface. Typical of these materials include ceramic and synthetic composition, many of which are proprietary in nature. The rotor element 41 is rotatably mounted to a shaft (not shown) which in turn is connected to a gear reduction inside the actuator body 55 (FIG. 1). The gear reduction is then coupled to the motor shaft of a conventional electric motor applied in shear valve or flat face valve technology.

Other additional instruments include a probe washing station 56 for washing and rinsing the probe tip after aspirating sample from the sample vial or well 48, and after the sample is ejected. This procedure prevents cross-contamination of the drawn samples.

Figure 5:
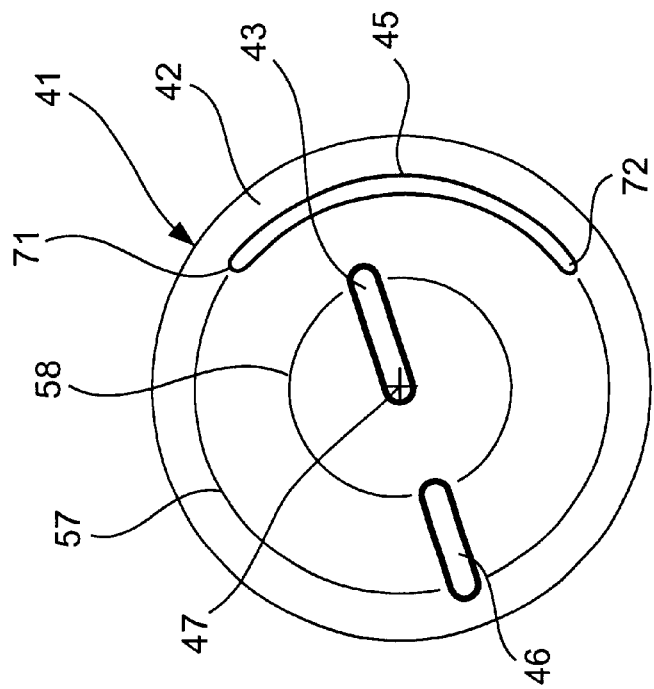
FIG. 5 is a top plan view of the rotor face of the rotor element. A "zero-thickness" slice of the face, viewed from the back of the rotor.
Figure 4:
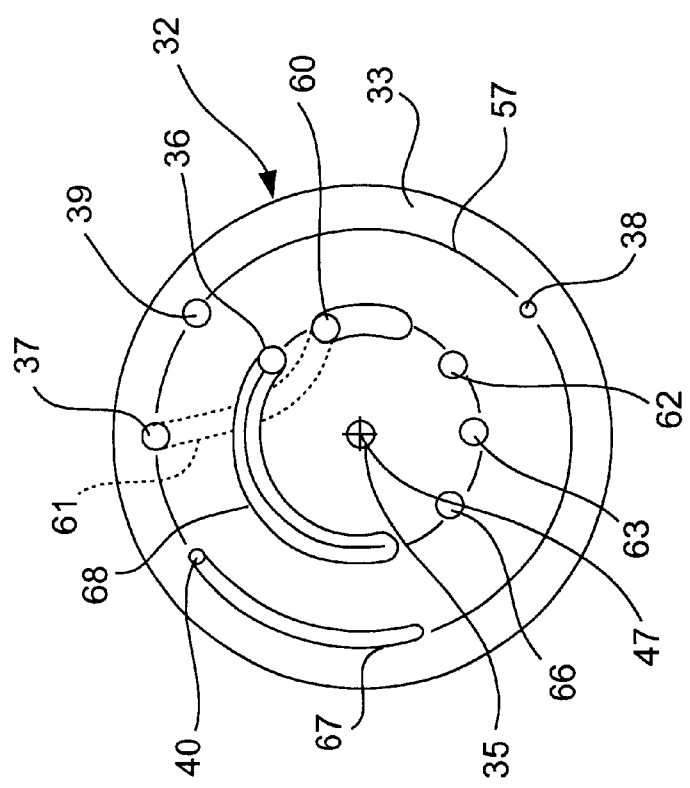
FIG. 4 is a top plan view of the stator face of the stator element.

As previously indicated, the switching functions to enable fluid communication channels for aspirating and injection a sample are performed by the rotor valve apparatus 20 which rotates the rotor element 41 relative the stator element 32 between the Load Position, the Overfill Position and the Injection Position to name a few. Referring now to FIGS. 4 and 5, a simplified view of the rotor face 42 and the stator face 33 is illustrated.

Briefly, the stator has ten (10) communication ports terminating at the stator face 33, many of which have already been defined. Centered at the rotational axis 47 is the metering port 35 which is fluidly coupled to the metering pump 22. Four other ports lie in an outer first imaginary circle 57 whose center is coincident with the axis of rotation 47. Clockwise, these include the exit port 40 which is fluidly coupled to the analyzing device 26; the loop upstream port 37 fluidly coupled to the upstream loop portion 27; the waste port 39 which is fluidly coupled to the waste depository (not shown), and the loop downstream port 38 fluidly coupled to the downstream loop portion 31. Five interior ports lie in an interior second imaginary circle 58 whose center is also coincident with the axis of rotation 47. As previously mentioned, the injection port 36 is fluidly coupled to the injection pump 23. This injection pump port 36 is also in radial alignment between the metering port 35 and the waste port 39. Clockwise from the injection port 36 is a connection port 60 fluidly connected to the loop upstream port 37 through an interior passage 61 in the stator element 32. The remaining ports include a fluid wash port 62 fluidly coupled to a probe wash and rinse station 56; a wash reservoir port 63 fluidly coupled to a reservoir 64 of wash fluid 65; and a flush port 66 fluidly coupled to the pump seals (not shown) of the injection pump 23.

In addition to the communication ports, the stator face 33 (FIG. 4) also defines three communication channels 67, 68 and 70 which extend about the rotational axis 47. A crescent-shaped first communication channel 67 lies in the first imaginary circle with one end in fluid communication with the exit port 40, and the other end extending counter-clockwise therefrom by an arc angle of about 72°. Thus, this communication channel enables continuous fluid communication with the analyzing device from multiple Rotor positions A–C. A crescent-shaped second communication channel 68 lies in the second imaginary circle 58 at an orientation substantially concentric with the first communication channel 67. One end is in fluid communication with the injection pump port 36, while the other end extends counter-clockwise therefrom by an arc angle of about 144°. Likewise, this second communication channel 68 enables the injection pump to maintain fluid communication with various components at multiple positions. Finally, a third communication channel 70 also lies in the second imaginary circle 58 with one end in fluid communication with the connection port 60, and the other end extending clockwise therefrom by an arc angle of about 36°.

Referring now to the rotor face 42, and as shown in FIG. 5, a first bridge channel 43 extending radially from the rotational axis 47 having one end lying at the central metering port 35 while the opposite end terminates at the second imaginary circle 58. This bridge channel 43 remains in continual fluid communication with the metering device at all positions. The rotor face 42 also defines a crescent-shaped second bridge channel 45 having both the one end 71 and the opposite other end 72 lying in the first imaginary circle 57. These opposed ends are preferably positioned apart by an arc angle of about 108°. Moreover, the entire second bridge channel preferably lies in the first imaginary circle 57. Lastly, the rotor face 42 defines a third bridge channel 46 in radial alignment with the first bridge channel 43, and extending radially from the second imaginary circle 58 to the first imaginary circle 57.

Figure 6:
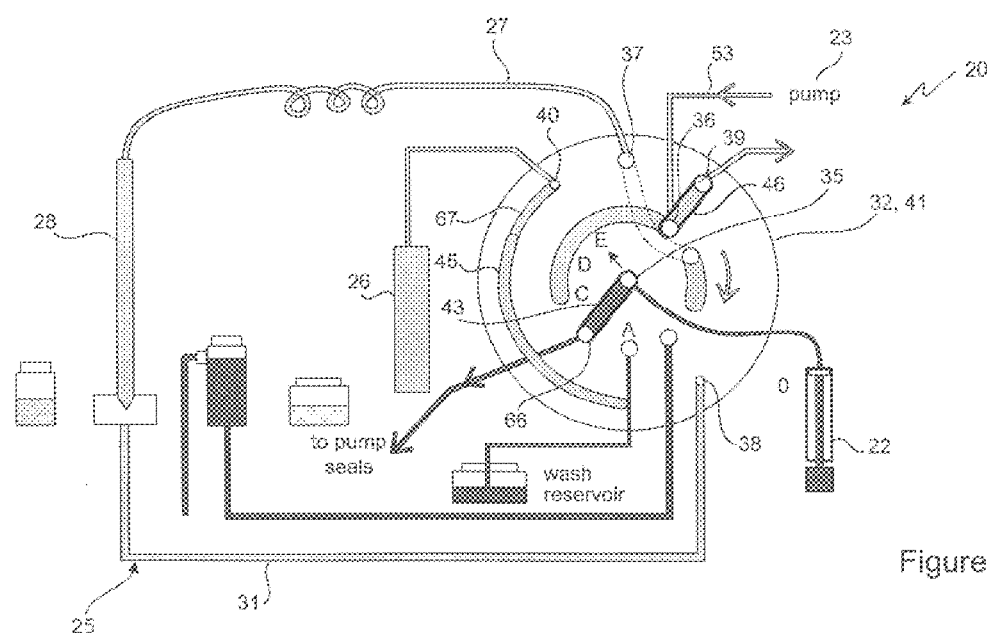
FIG. 6 is a schematic view of the rotor-stator interface illustrating a pump seal purge position of the sample injection valve of FIG. 1.
Figure 7:
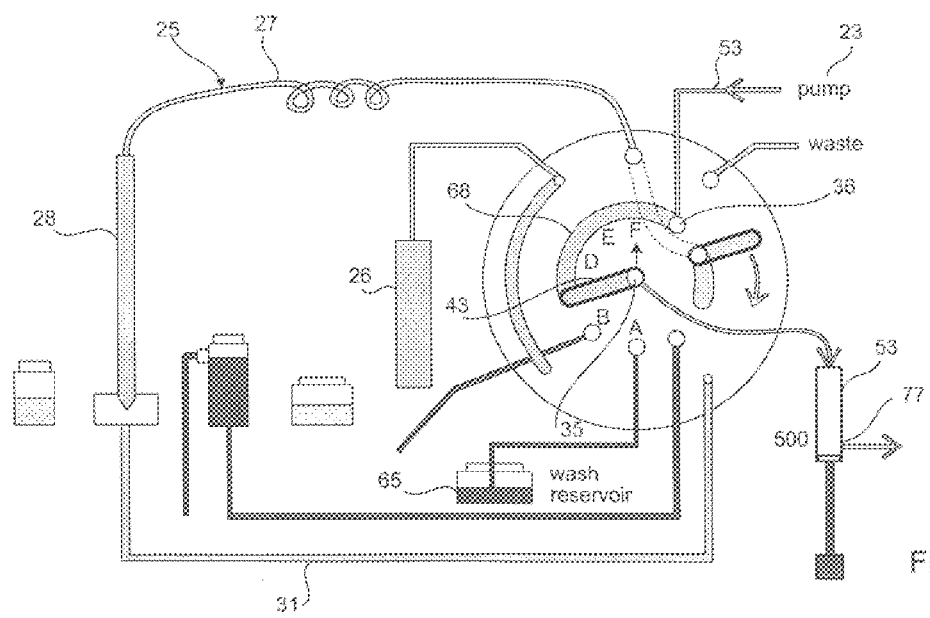
FIG. 7 is a schematic view of the rotor-stator interface illustrating a metering syringe purge position of the sample injection valve of FIG. 1.

Accordingly, as will be described in greater detail below, a 9-port, six position rotor valve apparatus 20 is provided with each position being angularly spaced apart by about 36°. Four rotor positions are dedicated to the load-wash-inject cycle (i.e., the Load Position, the Overfill Position, a Probe wash Position and the Injection Position), while a fifth position enables purging of the pump and piston seals (FIG. 6). A sixth position is dedicated to purging the metering pump 22 (FIG. 7).

Henceforth, the Partial-Fill and the Complete-Fill Modes will be described in detail simultaneously, since the operation is substantially the same except for addition of the Overfill Position (Rotor Position A (FIG. 3G)) in the Complete-Fill Mode. Thus, Referring back to FIG. 2A (Partial-Fill) and FIG. 3A (Complete-Fill), the rotor element 41 is oriented at an initial Standby Position A. Incidentally, as will be apparent, this rotor element orientation also enables the Over-fill Position in the "Complete-Fill" mode. The first bridge channel 43 and the second bridge channel fluidly couple the metering pump 22, which is preferably a 500 $\mu$L metering syringe, to the waste port 39. As shown, the flow path extends through the metering port 35, the first bridge channel 43, the connection port 60, the interior passage 61, the loop upstream port 37, the upstream loop portion, the probe 28, downstream loop portion 31, loop downstream port 38, and through the second bridge channel 45 to the waste port 39. Further, the third bridge channel 46 fluidly connects the injection pump 23 to the analyzing device, via the second communication channel 68 to the first communication channel 67.

The metering syringe is preferably initially filled with about 350 $\mu$L of washing fluid. The sample loop 25, probe 28, as well as from the injection pump 23 to the analyzing device are continuously fill with mobile phase fluid 53.

Turning now to FIG. 2B (Partial-Fill) and FIG. 3B (Complete-Fill), the rotor element 41 rotates 36° clockwise to position B or the Load Position, which seals off the downstream loop portion 31 from the waste port 39. This enable the probe 28 to be unseated from the docking station 30 without siphoning of the mobile phase fluid 53 from the downstream loop portion 31 of the sample loop 25. As shown, the third communication channel 70 in the stator face 33 maintains continuous fluid communication between the metering syringe 22 and the probe 28. Similarly, the first communication channel 67 and the concentric second communication channel 68 enable continuous fluid communication between the injection pump 23 and the analyzing device, via the third bridge channel 46. This continuous connection permits the constant flow of mobile phase fluid 53 from the injection pump 23 to the analyzing device. Such continuous flow is particularly important to continue the chromatography analysis for previous runs.

The probe is then undocked from the docking station 30, and moved, via positioner 51 (FIG. 1) to the sample vial 29 to draw sample 24. In the "Partial-Fill" mode, as shown in FIG. 2C, the metering syringe 22 is actuated to draw 5 $\mu$L of sample, for example, into the probe 28. Sample volumes using this mode can typically range from about 0.5 $\mu$L to about 50 $\mu$L.

In contrast, in the "Complete-Fill" mode, as shown in FIG. 3C, the metering syringe 22 is actuated to draw a substantially greater volume of sample into the probe 28 to overfill the downstream loop portion 31. In the example, about 50 $\mu$L of sample is drawn by the metering syringe 22. Thus, both the probe 28 and the upstream loop portion 27 must have sufficient capacity to withdraw and hold the sample therein. In the preferred embodiment, the capacity of the upstream loop portion 27 is about 500 $\mu$L which generally matches the capacity of the metering syringe. This ensures that the sample will not be withdrawn through the loop upstream port 37 and into the valve where it may be difficult to flush out.

To further ensure that only pure sample is utilized during overfilling of the downstream loop portion 31, an air segmenting bubble technique may be applied to improve precision. This is performed initially by positioning the probe tip 52 in the air, and retracting the metering syringe slightly to draw in an air bubble 73 into the tip of the probe 28. When the probe is subsequently immersed in the sample vial 29 for loading thereof, this air bubble 73 will separate the mobile phase fluid 53 from the drawn sample 24 to prevent intermixing.

After the sample has been loaded into the probe and/or upstream loop portion 27, the rotor valve apparatus 20 is rotated clockwise 36° to Rotor Position C or a Probe Tip Washing Position, in both the Partial and Complete-Fill Modes. As shown in FIG. 2D (Partial-Fill) and FIG. 3D (Complete-Fill), the rotor second bridge channel 45 remains sealed against the stator face 33 while the probe 28 is undocked. The first bridge channel 43 connects the metering port 35 to the fluid wash port 62 to fluidly couple the metering syringe 22 to the wash station 56. The third bridge channel 46 maintains continuous fluid communication between the injection pump 23 and the analyzing device 26 to continue analysis from previous runs.

The probe tip 52 is then submersed in the wash fluid 65 contained in the wash station 56. Washing of the probe tip 52 removes the sample contained on the outside thereof. This avoids or significantly reduces potential contamination of the docking station 30 which may thereby cause carry-over. First, within each injection cycle, the wash station 56 is flushed with fresh wash solvent and/or mobile phase so that there is no buildup of sample. Secondly, the outside of the probe is washed with flowing liquid. Moreover, the approximate 5 μL of mobile phase fluid (labeled "m" in FIG. 2E) overdrawn in the Load Position (FIG. 2C) in the "Partial-Fill" mode, and the approximate 50 μL of mobile phase fluid (labeled "m" in FIG. 3E) overdrawn in the Load Position (FIG. 3C) in the "Complete-Fill" mode can be expelled.

Initially, it may be desirable to draw a meniscus slightly into the probe 28 at the probe tip thereof prior to immersing in the wash fluid to avoid mixing of the sample therewith. Once the tip 52 is immersed, the metering syringe 22 is actuated to expel wash fluid therefrom, flowing wash fluid into the wash station and past the probe tip 52. If the wash station is designed as a conventional wash cup with an overflow to waste, as shown, the metering syringe 22 can simply rinse the wash cup with the fresh wash that remains in the syringe after the Load step. By way of example, about 155 μL is dispensed from the metering syringe 22, going from about 355 μL to about 200 μL in the "Partial-Fill" mode of FIGS. 2D, 2E, and about 200 μL in the "Complete-Fill" mode of FIG. 3D, 3E going from about 400 μL to about 200 μL.

This feature can be a user-selectable volume at a user-selectable flow rate. By adding rinse solvent to the rinse vessel each cycle, the concentration of the sample components washed from the probe tip will not build up in the rinse vessel. The volume available is to some extend determined by the sample volume selected, and the metering syringe capacity.

The wash station 56 could also be provided by a cylinder-type wash station with spray nozzles and a bottom drain. In this wash station arrangement, the metering syringe could deliver to the nozzles for a spray-wash action on the probe tip 52. Typical of this design is disclosed in our U.S. Pat. No. 6,155,123, entitled MULTIVALVING SAMPLE INJECTION SYSTEM and incorporated by reference in its entirety.

After sufficient washing of the probe tip, the positioner 51 moves the probe back to the docking station 30 for docking and sealing of the probe. This is performed in both the Partial-Fill and Complete-Fill Modes, as shown in FIGS. 2F and 3F.

Referring now to FIG. 3G, and only in the "Complete-Fill" mode, the rotor valve apparatus 20 rotates the rotor element counterclockwise about 72° back to Rotor Position A to the Overfill Position. The metering syringe 22 is then actuated to expel the wash fluid therefrom to load the downstream loop portion 31 with sample 24. As shown, the sample 24 is urged through the docking station 30 into the downstream loop portion 31, having a known interior volume, at least until the drawn sample flows through the loop downstream port 38. As the sample 24 flows into the crescent-shaped second bridge channel 45 toward the waste port 39, the downstream loop portion 31 will be completely filled with sample 24. However, to ensure volumetric precision, the second bridge channel 45 is also overfilled with sample 24 until the leading portion thereof flow through the waste port 39 to completely fill the downstream loop portion 31 and the second bridge channel, as a unit. Accordingly, the complete volume of sample to be analyzed is the collective interior volume of both the downstream loop portion 31 and the second bridge channel 45.

In "Complete-Fill" mode example of FIGS. 3A–3N, the collective interior volume of the downstream loop portion 31 and the second bridge channel 45 is about 5 μL. By actuating the metering syringe to expel about 25 μL, the collective interior volume of the downstream loop portion 31 and the second bridge channel 45 can be overfilled by about five (5) times. It will be appreciated, however, that this interior volume may be increased or decreased by replacing the downstream loop portion 31 with one having an interior volume with a greater or lesser capacity. Typically, the collective interior volumes can range from about 1 μL to about 20 μL.

During the overfill step, the air segmenting bubble 73 should not pass through the docking station. This boundary ensures that the mobile phase fluid 53 will not enter into the downstream loop portion 31 through the docking station 30. However, some of the wash fluid 65 will enter the upstream loop portion 27, displacing the mobile phase fluid.

To further ensure volumetric precision, the transverse cross-sectional area of both the second bridge channel 45 and the loop downstream port 38 are matched to reduce sample dispersion as it flows therethrough. In the preferred embodiment, the transverse cross-sectional area of the second bridge channel is in the range of about 0.05 mm$^2$ to about 0.07 mm$^2$. More preferably, the transverse cross-sectional area is about 0.06 mm$^2$, having a width of about 0.30 mm and a depth of 0.20 mm.

By comparison, the transverse cross-sectional area of the first bridge channel 43 and third bridge channel is in the range of about 0.14 mm$^2$ to about 0.18 mm$^2$, and more preferably, about 0.16 mm$^2$, having a width of about 0.45 mm and a depth of 0.35 mm.

Regarding the diameter of the loop downstream port 38, the transverse cross-sectional area should be dimensionally similar to that of the second bridge channel 45 to minimize dispersion. Accordingly, the cross-sectional area is in the range of about 0.06 mm$^2$ to about 0.08 mm$^2$, and more preferably, about 0.07 mm$^2$, having a diameter of about 0.30 mm.

When in the "Complete-Fill" mode, the rotor valve apparatus 20 rotates 36° clockwise back to position B (which incidentally orientation wise, is also the Load Position). As shown in FIG. 3H, and as indicated above, the third communication channel 70 in the stator face 33 again maintains continuous fluid communication between the metering syringe 22 and the probe 28 to continue the chromatography analysis for previous runs. The downstream loop portion 31 is again sealed-off from the waste port 39. This enables the probe 28 to be unseated from the docking station 30 without siphoning of the drawn sample 24 contained in the downstream loop portion 31 and the second bridge channel 45. Thus, the positioner 51 undocks the probe 28 from the docking station 30, and moves the probe to the sample waste container 76. The metering syringe 22 subsequently empties the remaining wash fluid contained therein, which also expels the remaining sample 24 contained in the probe 28 and/or upstream loop portion 27, as well as the air segment bubble 73. In the Complete-Fill example, this amounts to approximately 175 μL.

It will be noted that additional wash fluid 65 from the metering syringe 22 will be urged into the upstream loop portion 27. In most situations, the wash fluid 65 is the same or similar to the mobile phase fluid at the beginning of the gradient run to prevent disturbances to the analyzing device.

Subsequently, the probe 28 is redocked with the docking station, as shown in FIG. 3J. In both the Partial-Fill and Complete-Fill Modes, the docking of the probe can be tested for leaks at this seating interface, if desired. This is performed in Rotor Position B where the metering syringe 22 is advanced slightly and controllably to check for the absence of bubbles and probe-dock leaks. A micro pressure transducer (not shown) is required in the upstream loop portion 27 or syringe connection tubing. The metering syringe 22 must also still contain some fluid.

Turning back to FIG. 2F for the Partial-Fill Mode, and from FIG. 3J in the Complete-Fill Mode, the system can now commence analysis of the sample by injecting the drawn sample 24 through the analyzing device 26. In the Partial-Fill Mode, from the Rotor Position C of FIG. 2F, the rotor element 41 is rotated 36° clockwise to Rotor Position D or the Injection Position (FIG. 2G). By comparison, in the Complete-Fill Mode, from the position B of FIG. 3J, the rotor element 41 is rotated 72° clockwise to the Injection Position (FIG. 3K).

FIGS. 2G and 3K illustrate that in the Injection Position, the first bridge channel 43 fluidly couples the metering syringe 22 to the wash reservoir port 63, which in turn is fluidly coupled to the wash reservoir 64. One end of the crescent-shaped second bridge channel 45 is fluidly coupled to the loop downstream port 38, while the opposite other end is fluidly coupled to the other end of the crescent-shaped first communication channel of the stator face 33. Finally, the third bridge channel 46 of the rotor face 42 fluidly couples the injection pump 23 to the probe 28.

Accordingly, the injection pump 23 is fluidly coupled to the analyzing device 26 via the probe 28 to second bridge channel 45 to first communication channel 67. The drawn samples are subsequently entirely injected into the analyzing device 26. Typically, the injection pump 23 should dispel about 100 μl to about 300 μl more than the quantity of sample aspirated to assure emergence of the aspirated sample from the valve and into the analyzing device 26.

Similar to the crescent-shaped second bridge channel 45 and the loop downstream port 38, the transverse cross-sectional area of the first communication channel 67 and the exit port 40 are relatively narrow to reduce sample dispersion as the sample flows therethrough. In the preferred embodiment, the cross-sectional area of the first communication channel 67 is in the range of about 0.05 mm² to about 0.07 mm², and more preferably about 0.06 mm², having a width of about 0.30 mm and a depth of 0.20 mm. Similarly, the transverse cross-sectional area of the exit port 40 is in the range of about 0.06 mm² to about 0.08 mm², and more preferably, about 0.07 mm², having a diameter of about 0.30 mm.

Figure 2H:
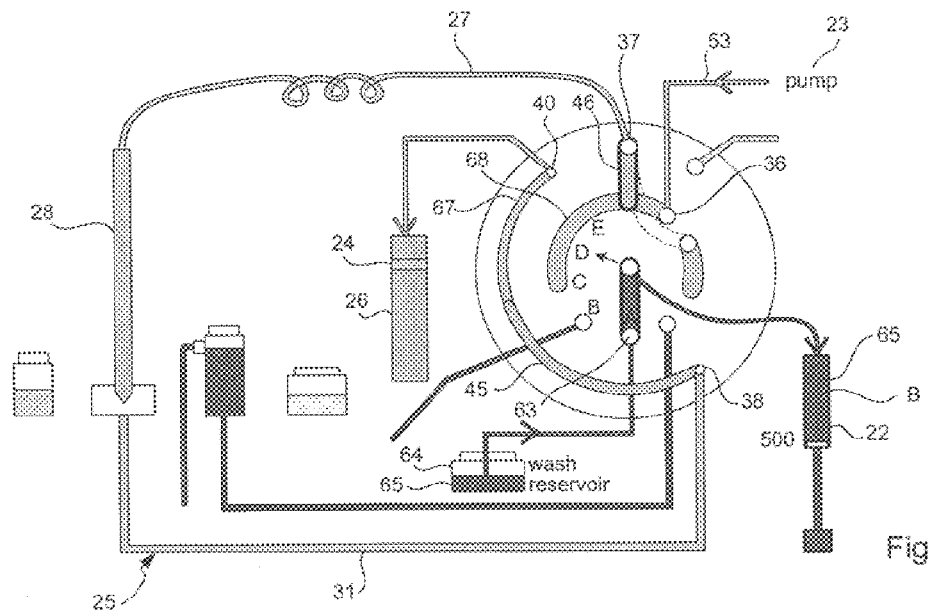
Figure 3L:
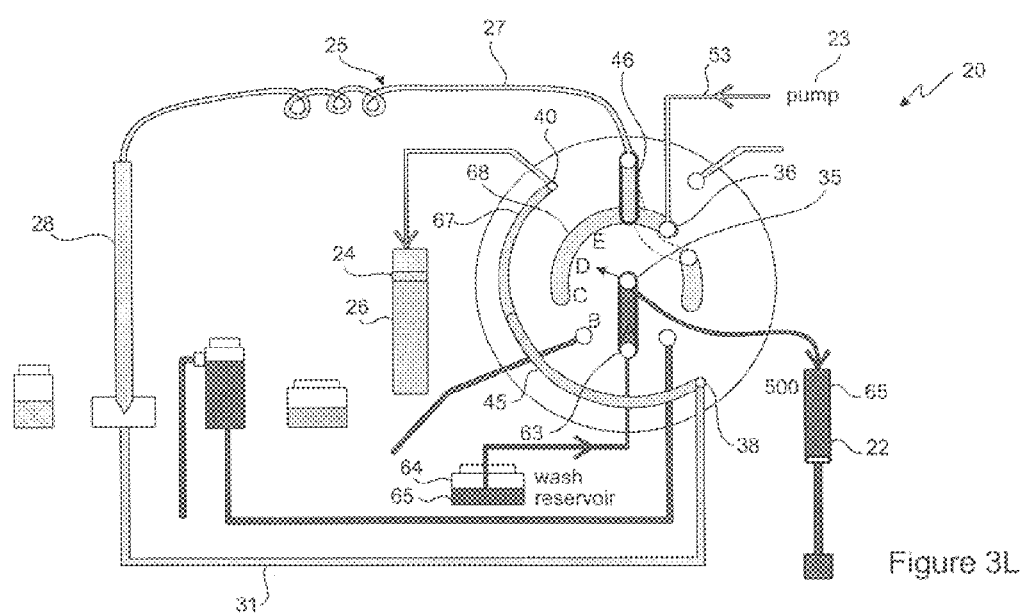

This switching arrangement also enables the metering syringe 22 to completely refill with wash fluid 65 from the wash reservoir 64 (FIGS. 2H and 3L). In both fill mode examples, the metering syringe 22 is refills about 500 μL of wash fluid 65. Preferably, the wash fluid 65 in the wash reservoir 64 should be degassed prior to a series of runs to minimize bubble formation in the metering syringe 22 since such formation significantly reduces volumetric precision.

This, however, is primarily only a concern in the Partial-Fill Mode. In the Complete-Fill Mode, small errors in the metering of the syringe volume will not affect the precision since it is determined only by the collective interior volume of the downstream loop portion 31 and the crescent-shaped second bridge channel 45.

Figure 2I:
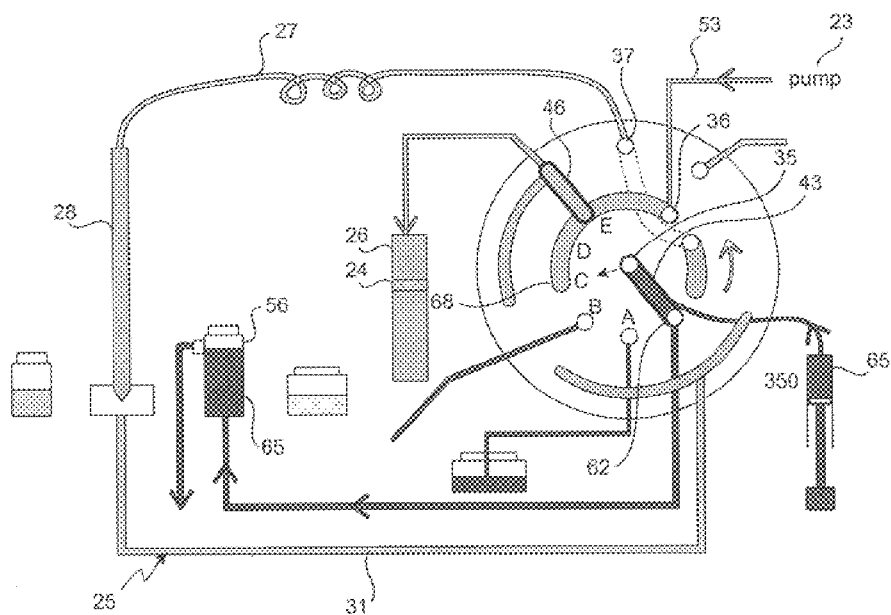
Figure 2J:
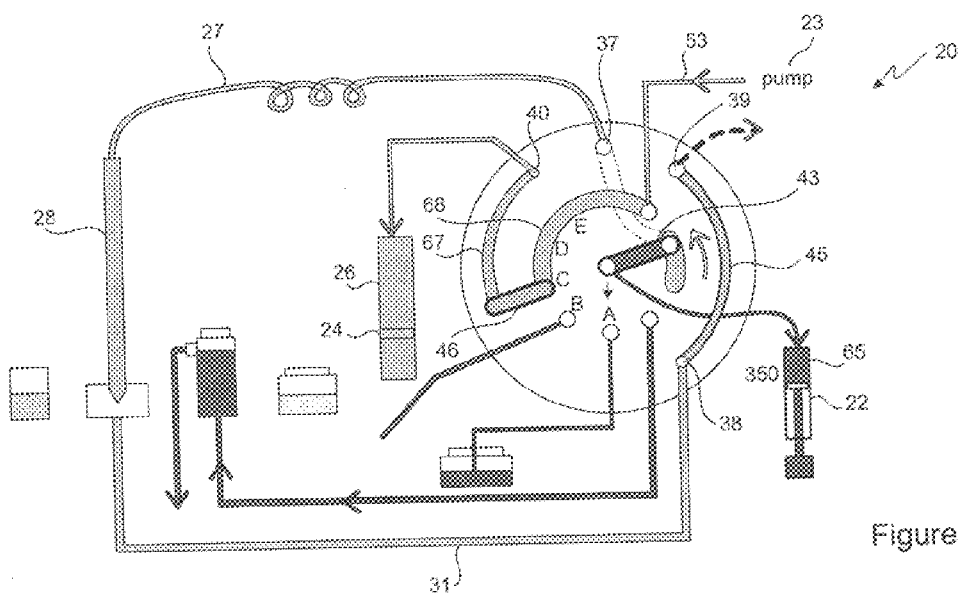

After injection of the sample into the analyzing device 26 and refilling of the metering syringe 22, the rotor element 41 is rotated 36° counter-clockwise back to Rotor Position C. As illustrated in FIG. 2I (Partial-Fill) and FIG. 3M (Complete-Fill), the upstream loop portion 27 and the downstream loop portion 31 are taken off-line. This is performed by sealing the stator upstream port 37 against the rotor face 42, while the stator downstream port 38 remains fluidly coupled to the second bridge channel 45, although this channel is out of fluid communication with both the waste port 39 and the first communication channel 67. Thus, since the probe remains docked in the docking station 30, the sample loop 25 remains pressurized, but without the flow of mobile phase fluid therethrough.

Figure 3M:
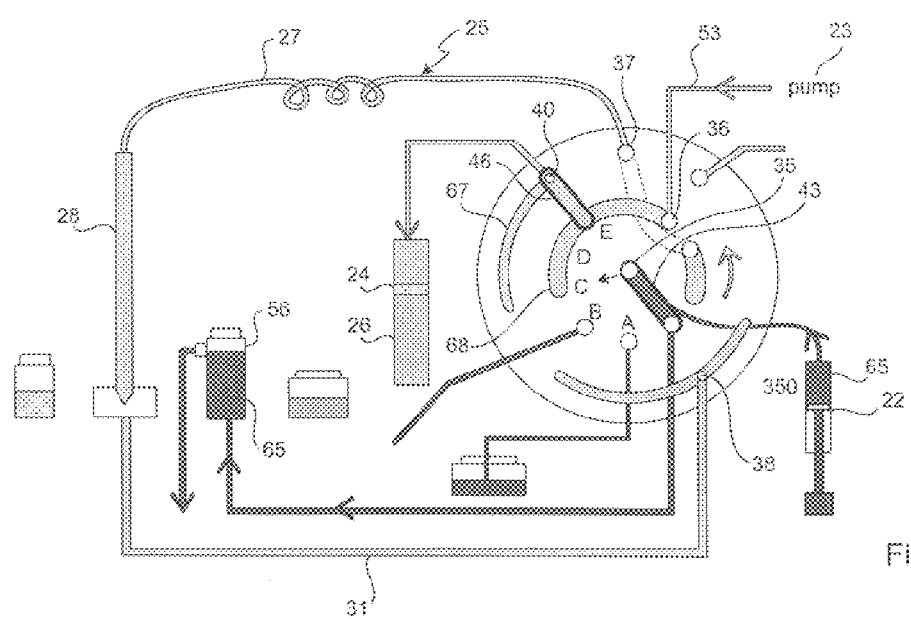
Figure 3N:
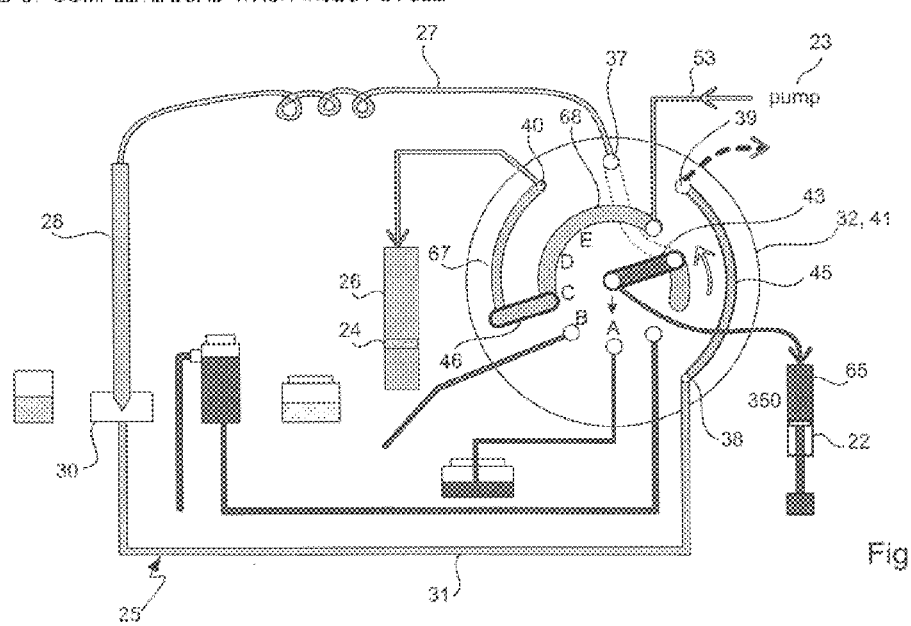

FIGS. 2I and 3M further illustrate that in Rotor Position C, the first bridge channel 43 connects the metering port 35 to the fluid wash port 62 to fluidly recouple the metering syringe 22 to the wash station 56. The third bridge channel 46 maintains continuous fluid communication between the injection pump 23 and the analyzing device 26 to continue analysis by now pumping mobile phase fluid 53 through the analyzing device.

The metering syringe 22 dispenses fresh wash fluid into the wash station 56 for replenishment thereof. In these examples, the metering syringe delivers about 150 μl to the wash station, leaving about 350 μl in the syringe.

To complete the wash cycle, rotor element 41 rotates counter clockwise 72° back to Rotor Position A where the injection pump 23 remains fluidly coupled to the analyzing device 26 to continue analysis, while the metering syringe 22 is fluidly coupled to the waste port 39, via the first bridge channel 43 to upstream loop portion 27 to probe 28 to downstream loop portion 31 to second bridge channel 45. During rotation of the rotor element through Rotor Position B from position C to position A (i.e., from FIGS. 2I to 2J, and 3M to 3N), the metering syringe 22 is fluidly coupled to the pressurized upstream loop portion 27 (via the first bridge channel 43) before the fluid connection of the downstream loop portion 31 to the waste port 39. This momentarily (about 100 msec) exposes the metering syringe 22 to the high pressure of the upper loop portion 27 which absorbs the volume change. Alternatively, the pressure shock may be relieved by undocking the probe 28 from the docking station 30 before rotation from Rotor Position C to Rotor Position B. Typically, about 1 μl to about 4 μl of fluid would be deposited onto the docking surface.

In accordance with another aspect of the present invention, the multi-function valve apparatus 20 can be rotated to Rotor Position E or a Pump Seal Purge Position. As shown in FIG. 6, the third bridge channel 46 of the rotor element 41 fluidly couples the injection pump directly to the waste port 39. This allows a high flow rate purging of the injection pump 23. This feature is highly beneficial when it is desirable to change the mobile phase fluid to one appropriate for a new series of analysis (i.e., when changing methods). This feature can often replace a separate motorized valve which performs this flushing at the end of a series of analyses, preparing the analyzing device for the next series of analyses. Ideally, this purge may commence automatically without operator intervention.

In this Rotor Position, both the analyzing device 26 and the sample loop 25 are kept off-line. The first bridge channel 43 also fluidly couples the metering port 35 to the flush port 66, which in turn, is in fluid communication with a seal-wash chamber (not shown) of the injection pump 23. This allows flushing and cleaning of the region where the pump pistons enter the high pressure seals of the pump chamber pump seals to be flushed and cleaned of any debris or salt buffers. Such periodic flushing prevents the salts from crystallizing and potentially scoring the pump seals upon restart on the next cycle. Moreover, this purge is preferably performed while the pump is running. Flushing of the pump seals is most efficient while the pump is running, and since the injection pump 23 is purging to the waste port 39 at a high flow rate, the flush is more efficient.

The metering syringe can be filled and refilled with freshly degassed solvent or wash fluid 65 from the wash reservoir by alternately filling and purging the metering syringe. This is performed by cycling the rotor valve between Rotor Positions D and E.

Referring now to FIG. 7, the multi-function valve apparatus 20 can be rotated to a last Rotor Position F or a Metering Syringe Purge Position. Again, both the analyzing device 26 and the sample loop 25 are kept off-line. The first bridge channel 43 of the rotor element 41, however, fluidly couples the injection pump 23 directly to the metering syringe 22, via the second communication channel 68. This allows the injection pump 23 to supply the metering syringe 22 with currently degassed mobile phase fluid for purging thereof. To perform this procedure, the metering syringe 22 must have a rear side port 77 that allows the flow therethrough or if there is a tee at the syringe inlet (not shown) and a solenoid control valve that opens. This configuration permits the flow to pass to a drain while the metering syringe 22 is reciprocated back and forth, sampling the passing of the mobile phase fluid.

Again, the metering syringe can be refilled with freshly degassed solvent or wash fluid 65 from the wash reservoir by cycling the rotor valve between Rotor Positions F and D.

Although only a few embodiments of the present inventions have been described in detail, it should be understood that the present inventions may be embodied in many other specific forms without departing from the spirit or scope of the inventions.

What is claimed is:

1. A multi-function valve apparatus for use with a Probe-In-Loop (PIL) architecture sample injection assembly, having a metering pump and an injection pump, to direct a Partial-Fill or a Complete-Fill of sample into a sample loop assembly, and to inject the sample from the sample loop into an analyzing device, said sample loop assembly including an upstream loop portion coupled between the valve apparatus and a probe configured to aspirate and dispense the sample into a dock, and a downstream loop portion having an interior volume and coupled between the dock and the valve apparatus, said valve apparatus comprising:
    a stator element having a stator face defining a metering port fluidly coupled to the metering pump; an injection pump port fluidly coupled to the injection pump, a loop upstream port fluidly coupled to the upstream loop portion, a loop downstream port fluidly coupled to the downstream loop portion, an exit port fluidly coupled to the analyzing device and a waste port; and
    a rotor including a rotor face in fluid-tight contact against said stator face, said rotor face having a first bridge channel, a second bridge channel defining a discrete volume with the stator face, and a third bridge channel, said rotor face being rotatable about a rotation axis relative the stator between:
    a Load Position wherein said first bridge channel fluidly couples the metering port to the sample loop upstream port enabling the probe to aspirate a discrete volume of sample into the probe, during a Partial-Fill Mode, or a second volume of sample into the probe, during a Complete-Fill Mode;
    an Overfill Position, in the Complete-Fill Mode, wherein the second bridge channel fluidly couples the sample loop downstream port to the waste port, and the first bridge channel fluidly couples the metering port to the sample loop upstream port enabling the metering pump, when the probe is docked in the dock, to dispense the sample from the probe into the downstream loop portion, out of the downstream port, into the second bridge channel and out the waste port to completely fill the downstream loop portion and the second bridge channel with a substantially precise known volume; and
    an Injection Position wherein the second bridge channel fluidly couples the sample loop downstream port to the exit port, and the third bridge channel fluidly couples the injection pump port to the sample loop upstream port enabling the injection pump, when the probe is docked in the dock, to inject the discrete volume of sample, in the Partial-Fill Mode, or the precise known volume of sample, in the Complete-Fill Mode, into the analyzing device.

2. The valve apparatus as defined by claim 1, wherein said waste port, said upstream port and the exit port lie on a first imaginary circle that is concentric with said rotation axis, and
the ends of said second bridge channel further lying on said imaginary circle such that, in the Overfill Position, one end fluidly connects to the waste port and the other end fluidly connects to the loop downstream port, and such that, in the Injection Position, the other end fluidly connects to the loop downstream port and the one end fluidly connects to the exit port.

3. The valve apparatus as defined by claim 2, wherein said second bridge channel includes a relatively small transverse cross-sectional area to minimize dispersion.

4. The valve apparatus as defined by claim 3, wherein said second bridge channel is of a transverse cross-sectional area from about 0.05 mm$^2$ to about 0.07 mm$^2$.

5. The valve apparatus as defined by claim 2, wherein said second bridge channel lies in said first imaginary circle.

6. The valve apparatus as defined by claim 2, wherein said stator face further defines a first communication channel having one end in fluid communication with the exit port and the other end lying on the first imaginary circle such that, in the Injection Position, said other end being in fluid communication with the other end of the second bridge channel.

7. The valve apparatus as defined by claim 6, wherein said second bridge channel and the first communication channel lie in said first imaginary circle.

8. The valve apparatus as defined by claim 7, wherein said second bridge channel and said first communication channel have relatively small transverse cross-sectional areas to minimize dispersion.

9. The valve apparatus as defined by claim 6, wherein said third bridge channel fluidly couples the injection pump port to the exit port enabling the injection pump to purge the analyzing device in a fourth valve position.

10. The valve apparatus as defined by claim 9, wherein said first communication channel lies in said first imaginary circle, said injection pump port lies in a second imaginary circle, said stator face further defines a second communication channel lying in said second imaginary circle and having one end in fluid communication with the injection port, and said third bridge channel extending radially from said rotational axis and fluidly coupling said first communication channel to said second communication channel to enable the injection pump to purge the analyzing device continuously during rotational movement of the valve apparatus from the Overfill Position, the Load Position and to the fourth valve position.

11. The valve apparatus as defined by claim 10, wherein in said Injection Position, said third bridge channel fluidly couples said second communication channel to said loop upstream port.

12. The valve apparatus as defined by claim 10, wherein in a fifth valve position, said third bridge channel fluidly couples said injection pump port to said waste port.

13. The valve apparatus as defined by claim 12, wherein in the fifth valve position, said first bridge channel fluidly couples said metering port to a pump seals port to fluidly couple the metering pump to the pump seals of the injection pump for cleaning thereof.

14. The valve apparatus as defined by claim 1, wherein in a fifth valve position, said first bridge channel fluidly couples said metering port to a pump seals port to fluidly couple the metering pump to the pump seals of the injection pump for cleaning thereof.

15. The valve apparatus as defined by claim 14, wherein said metering port is centrally positioned substantially at said rotational axis, and said first bridge channel extends radially outward from said rotational axis.

16. The valve apparatus as defined by claim 1, wherein in the Load Position, said loop downstream port is fluidly sealed from both the waste port and the exit port.

17. The valve apparatus as defined by claim 1, wherein said metering port is centrally positioned substantially at said rotational axis, and said first bridge channel extends radially outward from said rotational axis.

18. The valve apparatus as defined by claim 17, wherein in the Injection Position, said first bridge channel fluidly couples the said metering port to a fluid reservoir port to fluidly couple the metering pump to a fluid reservoir of fluid to fill the metering pump.

19. A Probe-In-Loop (PIL) architecture sample injection assembly comprising:

a rotor valve assembly including a stator element having a stator face defining an injection pump port, a metering port, a loop upstream port, a loop downstream port, an exit port and a waste port, and a rotor element having a rotor face in fluid-tight contact against said stator face, and defining at least one bridge channel;

an injection pump fluidly coupled to the stator injection pump port for supplying mobile phase fluid;

a metering pump fluidly coupled to the stator metering port for supplying or withdrawing metered mobile phase fluid;

an analyzing device fluidly coupled to the stator exit port;

a PIL sample loop assembly having a docking station, a probe, an upstream loop portion fluidly coupling the loop upstream port of the stator element to the probe to aspirate sample into the probe and dispense the aspirated sample from the probe into the docking station, and a downstream loop portion fluidly coupling the docking station to the loop downstream port of the stator element, said downstream loop portion having a discrete interior volume between the docking station and the loop downstream port;

said rotor element being rotatable about a rotation axis to rotate the rotor face relative the stator face between:

a Load Position fluidly coupling the metering port to the sample loop upstream port enabling the probe to aspirate one of a discrete volume of sample into the probe, during a Partial-Fill Mode, and a second volume of sample into the probe, during a Complete-Fill Mode;

an Overfill Position, in the Complete-Fill Mode, fluidly coupling the sample loop downstream port to the waste port, and the metering port to the sample loop upstream port enabling the metering pump, when the probe is docked in the docking station, to dispense the aspirated sample from the probe into the downstream loop portion, and out of the loop downstream port toward the waste port to completely fill the downstream loop portion a substantially precise known volume; and an Injection Position fluidly coupling the sample loop downstream port to the stator exit port, and the stator injection pump port to the sample loop upstream port enabling the injection pump, when the probe is docked in the docking station, to inject the discrete volume of sample, in the Partial-Fill Mode, or the precise known volume of sample, in the Complete-Fill Mode, into the analyzing device.

20. The sample injection assembly as defined by claim 19, wherein said rotor face having a first bridge channel wherein, in the Load Position, said first bridge channel fluidly couples the metering port to the sample loop upstream port.

21. The sample injection assembly as defined by claim 20, wherein said rotor face having a second bridge channel defining a discrete volume with the stator face, wherein, in the Overfill Position the second bridge channel fluidly couples the sample loop downstream port to the waste port, and the first bridge channel fluidly couples the metering port to the sample loop upstream port enabling the metering pump, when the probe is docked in the dock, to further dispense the sample from the probe into the downstream loop portion, out of the loop downstream port, into the second bridge channel and out the waste port to completely fill the downstream loop portion and the second bridge channel with the substantially precise known volume.

22. The sample injection assembly as defined by claim 21, wherein said rotor face having a third bridge channel wherein, in Injection Position, the second bridge channel fluidly couples the sample loop downstream port to the stator exit port, and the third bridge channel fluidly couples the stator injection pump port to the sample loop upstream port.

23. The sample injection assembly as defined by claim 22, wherein said waste port, said upstream port and the exit port lie on a first imaginary circle that is concentric with said rotation axis, and the ends of said second bridge channel further lying on said imaginary circle such that, in the Overfill Position, one end fluidly connects to the waste port and the other end fluidly connects to the loop downstream port, and such that, in the Injection Position, the one end fluidly connects to the loop downstream port and the other end fluidly connects to the exit port.

24. The sample injection assembly as defined by claim 19, wherein said waste port, said upstream port and the exit port lie on a first imaginary circle that is concentric with said rotation axis, and the ends of said second bridge channel further lying on said imaginary circle such that, in the Overfill Position, one end fluidly connects to the waste port and the other end fluidly connects to the loop downstream port, and such that, in the Injection Position, the one end fluidly connects to the loop downstream port and the one end fluidly connects to the exit port.

25. The sample injection assembly as defined by claim 24, wherein said stator face further defines a first communication channel having one end in fluid communication with the exit port and the other end lying on the first imaginary circle such that, in the Injection Position, said other end being in fluid communication with the other end of the second bridge channel of the rotor.

26. The sample injection assembly as defined by claim 25, wherein said second bridge channel and the first communication channel lie in said first imaginary circle.

27. The sample injection assembly as defined by claim 26, wherein said second bridge channel and said first communication channel have relatively small transverse cross-sectional areas to minimize dispersion.

28. The sample injection assembly as defined by claim 25, wherein said third bridge channel fluidly couples the injection pump port to the exit port enabling the injection pump to purge the analyzing device in a fourth valve position.

29. The sample injection assembly as defined by claim 28, wherein said first communication channel lies in said first imaginary circle, said injection pump port lies in a second imaginary circle, said stator face further defines a second communication channel lying in said second imaginary circle and having one end in fluid communication with the injection port, and said third bridge channel extending radially from said rotational axis and fluidly coupling said first communication channel to said second communication channel to enable the injection pump to purge the analyzing device continuously during rotational movement of the sample injection assembly from the Overfill Position, the Load Position and to the fourth valve position.

30. The sample injection assembly as defined by claim 29, wherein in a fifth valve position, said third bridge channel fluidly couples said injection pump port to said waste port.

31. The sample injection assembly as defined by claim 22, wherein in a fifth valve position, said first bridge channel fluidly couples said metering port to a pump seals port to fluidly couple the metering pump to the pump seals of the injection pump for cleaning thereof.

32. The sample injection assembly as defined by claim 31, wherein said metering port is centrally positioned substantially at said rotational axis, and said first bridge channel extends radially outward from said rotational axis.

33. The sample injection assembly as defined by claim 22, wherein said metering port is centrally positioned substantially at said rotational axis, and said first bridge channel extends radially outward from said rotational axis.

34. The sample injection assembly as defined by claim 33, further including:

a fluid reservoir fluidly coupled to a fluid reservoir port on said stator face, and in the Injection Position, said first bridge channel fluidly couples said metering port to fluid reservoir port, fluidly coupling the metering pump to the fluid reservoir, to fill the metering pump with fluid therefrom.

35. The sample injection assembly as defined by claim 33, further including:

a wash station adapted for receipt of the tip of the probe therein when unlocked from the dock, and fluidly coupled to a fluid wash port on said stator face, and in a fourth valve position, said first bridge channel fluidly couples said metering port to the fluid wash port, fluidly coupling the metering pump to the wash station to flow fluid past the tip of the probe therein.

36. The sample injection assembly as defined by claim 28, further including:

a wash station adapted for receipt of the tip of the probe therein when unlocked from the dock, and fluidly coupled to a fluid wash port on said stator face, and in the fourth valve position, said first bridge channel fluidly couples said metering port to the fluid wash port, fluidly coupling the metering pump to the wash station to flow fluid past the tip of the probe therein.

37. A method of transferring sample from a sample source to an analyzing device using multi-function valve apparatus for use with a Probe-In-Loop (PIL) architecture sample injection assembly to direct a Partial-Fill or a Complete-Fill of the sample into a sample loop assembly, and to inject the sample from the sample loop assembly into the analyzing device, said sample loop assembly including an upstream loop portion coupled between the valve apparatus and a probe configured to aspirate and dispense the sample into a dock, and a downstream loop portion having an interior volume and coupled between the dock and the valve, said method comprising:

providing a stator element having a stator face defining a loop upstream port fluidly coupled to the end of the upstream loop portion, a loop downstream port fluidly coupled to the end of the downstream loop portion, an exit port fluidly coupled to the analyzing device and a waste port;

providing a rotor including a rotor face in fluid-tight contact against said stator face, and having a second bridge channel defining a discrete volume with the stator face, said rotor face being rotatable about a rotation axis relative the stator;

loading a discrete volume of sample through the probe, in a Partial-Fill Mode, and a second volume of sample through the probe, in a Complete-Fill Mode;

in the Complete-Fill Mode when the probe is docked in the dock, fluidly coupling the sample loop downstream port to the waste port through the second bridge channel of the rotor, and dispensing a portion of the sample from the probe though the dock and into the downstream loop portion, out of the downstream port, into the second bridge channel and out the waste port to completely fill the downstream loop portion and the second bridge channel with a substantially precise known volume;

fluidly coupling the sample loop downstream port to the exit port; and injecting the discrete volume of sample, in the Partial-Fill Mode, or the precise known volume of sample, in the Complete-Fill Mode, into the analyzing device.

* * * * *